United States Patent
Azizoglu et al.

(10) Patent No.: US 9,797,893 B2
(45) Date of Patent: *Oct. 24, 2017

(54) RAPID DETECTION OF ANALYTES IN LIQUID SAMPLES

(71) Applicant: Advanced Animal Diagnostics, Inc., Durham, NC (US)

(72) Inventors: Reha O. Azizoglu, Morrisville, NC (US); Stefano Bresolin, Garner, NC (US); David A. Calderwood, Chapel Hill, NC (US); Robert L. Cheek, Mebane, NC (US); Joy Parr Drach, Pontiac, IL (US); John Groelke, Raleigh, NC (US); Tobias M. Heineck, Durham, NC (US); Mitchell Hockett, Raleigh, NC (US); David Newcomb, Morrisville, NC (US); Duane Olsen, Hillsborough, NC (US); Chris Paul, Hillsborough, NC (US); Jasper N. Pollard, Durham, NC (US); Rodolfo R. Rodriguez, Cary, NC (US); Demetris Young, Durham, NC (US)

(73) Assignee: Advanced Animal Diagnostics, Inc., Durham, NC (US)

( * ) Notice: Subject to any disclaimer, the term of this patent is extended or adjusted under 35 U.S.C. 154(b) by 7 days.

This patent is subject to a terminal disclaimer.

(21) Appl. No.: 14/274,086

(22) Filed: May 9, 2014

(65) Prior Publication Data

US 2014/0363882 A1    Dec. 11, 2014

Related U.S. Application Data

(60) Provisional application No. 61/821,486, filed on May 9, 2013.

(51) Int. Cl.
  *G01N 35/04*  (2006.01)
  *G01N 35/02*  (2006.01)
  (Continued)

(52) U.S. Cl.
  CPC . *G01N 33/54366* (2013.01); *G01N 33/56911* (2013.01); *G01N 33/56938* (2013.01); *G01N 2333/30* (2013.01)

(58) Field of Classification Search
  CPC ....... G01N 33/54366; G01N 33/56911; G01N 33/56938; G01N 233/30
  See application file for complete search history.

(56) References Cited

U.S. PATENT DOCUMENTS 3,574,064 A * 4/1971 Binnings et al. ........... G01N 35/00029
                                                    222/416
3,883,247 A   5/1975 Adams
(Continued)

FOREIGN PATENT DOCUMENTS

EP    1 965 209        9/2008
EP    1 975 618 A1    10/2008
(Continued)

OTHER PUBLICATIONS

Xiao, Yan, and Siugong Gao. "Use of IgY antibodies and semiconductor nanocrystal detection in cancer biomarker quantitation", Biomakers in Medicine, (2010), 4;2:227-239.
(Continued)

*Primary Examiner* — Robert Eom
(74) *Attorney, Agent, or Firm* — Myers Bigel, P.A.

(57) ABSTRACT

A device for detecting at least one analyte in a liquid sample generally comprises (i) a support having a chamber for receiving a biological fluid (e.g., milk) therein, wherein said chamber is an elongate chamber having a length axis; (ii) a
(Continued)

(stationary or movable) carrier (in some embodiments in the form of an end cap, or connected to an end cap; in other embodiments in the form of an agitator in said elongate chamber).

2 Claims, 14 Drawing Sheets

(51) Int. Cl.
*G01N 33/543* (2006.01)
*G01N 33/569* (2006.01)

(56) References Cited

U.S. PATENT DOCUMENTS

| | | |
|---|---|---|
| 4,440,301 A | 4/1984 | Intengan |
| 4,946,266 A | 8/1990 | Kraft et al. |
| 5,132,210 A | 7/1992 | Adams et al. |
| 5,367,401 A * | 11/1994 | Saulietis .......... G01N 35/00029 356/246 |
| 5,494,829 A | 2/1996 | Sandstrom et al. |
| 5,620,845 A | 4/1997 | Gould et al. |
| 5,932,872 A | 8/1999 | Price |
| 6,057,166 A | 5/2000 | Childs et al. |
| 6,248,596 B1 | 6/2001 | Durst et al. |
| 6,322,963 B1 | 11/2001 | Bauer |
| 6,627,621 B2 | 9/2003 | Nagaoka et al. |
| 6,750,006 B2 | 6/2004 | Powers et al. |
| 6,790,661 B1 | 9/2004 | Goodnow |
| 7,027,628 B1 | 4/2006 | Gagnon et al. |
| 7,141,773 B2 | 11/2006 | Kaplan et al. |
| 7,390,997 B2 | 6/2008 | Tohma |
| 7,566,533 B2 | 7/2009 | Jacobs et al. |
| 7,589,962 B1 | 9/2009 | Bhatia |
| 7,749,775 B2 | 7/2010 | Maher et al. |
| 7,855,051 B2 | 12/2010 | Anderson et al. |
| 7,861,768 B1 | 1/2011 | Ghantiwala |
| 7,898,673 B2 | 3/2011 | Randers-Pehrson et al. |
| 7,932,093 B2 | 4/2011 | Renuart et al. |
| 7,943,153 B1 | 5/2011 | Leonard et al. |
| 8,021,848 B2 | 9/2011 | Straus |
| 8,067,246 B2 | 11/2011 | Marlborough et al. |
| 9,052,315 B2 | 6/2015 | Rodriguez et al. |
| 2001/0036645 A1 | 11/2001 | McNeirney et al. |
| 2001/0041347 A1 | 11/2001 | Sammak et al. |
| 2002/0098588 A1 | 7/2002 | Sammak et al. |
| 2002/0187485 A1 | 12/2002 | Jakobsen et al. |
| 2003/0127609 A1 | 7/2003 | El-Hage et al. |
| 2003/0206296 A1 | 11/2003 | Wolleschensky et al. |
| 2004/0101826 A1 | 5/2004 | Jones et al. |
| 2004/0101912 A1 | 5/2004 | Rubin et al. |
| 2004/0115624 A1 | 6/2004 | Wolde-Mariam |
| 2004/0208350 A1 | 10/2004 | Rea et al. |
| 2005/0068614 A1 | 3/2005 | Yoneyama et al. |
| 2005/0260695 A1 | 11/2005 | Fleming et al. |
| 2006/0068412 A1 | 3/2006 | Tang et al. |
| 2006/0134796 A1 | 6/2006 | Bommarito et al. |
| 2007/0015151 A1 | 1/2007 | Schrenzel et al. |
| 2007/0178606 A1 | 8/2007 | Imoarai et al. |
| 2007/0190566 A1 | 8/2007 | Montagu |
| 2007/0192882 A1 | 8/2007 | Dewald |
| 2007/0242349 A1 | 10/2007 | Tafas |
| 2007/0287147 A1 | 12/2007 | Nagamune et al. |
| 2008/0088918 A1 | 4/2008 | O'Connell |
| 2008/0220539 A1 | 9/2008 | Brauner et al. |
| 2008/0259566 A1 | 10/2008 | Fried |
| 2008/0274538 A1 | 11/2008 | Mutz et al. |
| 2009/0042814 A1 | 2/2009 | Petyaev et al. |
| 2009/0061507 A1 | 3/2009 | Ho |
| 2009/0068759 A1 | 3/2009 | Arenas et al. |
| 2009/0116101 A1 | 5/2009 | Tafas et al. |
| 2009/0233329 A1 | 9/2009 | Rodriguez et al. |
| 2010/0118394 A1 | 5/2010 | Hecker |
| 2010/0135861 A1 | 6/2010 | Sage et al. |
| 2010/0210022 A1 | 8/2010 | Madura |
| 2010/0227333 A1 | 9/2010 | Horowitz |
| 2010/0254854 A1 | 10/2010 | Rich et al. |
| 2010/0255601 A1 | 10/2010 | Beaudet et al. |
| 2010/0279310 A1 | 11/2010 | Sia et al. |
| 2010/0328766 A1 | 12/2010 | Griffin et al. |
| 2011/0003310 A1 | 1/2011 | Ennis et al. |
| 2011/0090326 A1 | 4/2011 | Kenny et al. |
| 2011/0117025 A1 | 5/2011 | Dacosta et al. |
| 2012/0020537 A1 | 1/2012 | Garcia et al. |
| 2012/0082361 A1 | 4/2012 | Burke et al. |
| 2014/0009596 A1 * | 1/2014 | Bresolin ............... G06T 7/0012 348/79 |

FOREIGN PATENT DOCUMENTS

| | | |
|---|---|---|
| JP | 2011-004654 A | 1/2011 |
| WO | WO 2004/097412 | 11/2004 |
| WO | WO 2008/002563 A2 | 1/2008 |
| WO | WO 2008/021862 | 2/2008 |
| WO | WO 2009/013683 | 1/2009 |
| WO | WO 2009/105711 | 8/2009 |
| WO | WO 2010/013335 A1 | 2/2010 |
| WO | WO 2011/113569 | 9/2011 |
| WO | WO 2012/051372 | 4/2012 |
| WO | WO 2012/094625 | 7/2012 |

OTHER PUBLICATIONS

Elert et al. Diameter of a Yeast, The Physics Factbook, 2000, Retrieved from the internet on Nov. 22, 2013 at URL http://hypertextbook.com/facts/2000/JennyNg.shtml.

Fischer J.E. et al. "Autofokus zur schnellen Verarbeitung mikroskipischer Praeparate", Informatik Fachberichte—Mustererkennung 1991, 13, DAGM Symposium Proceedings, Munchen, Oct. 9-11, 19991, vol. 290, Oct. 9, 1991, pp. 367-372.

Geusebroek et al. "Robust autofocusing in microscopy", Cytometry, vol. 39, Feb. 2000, pp. 1-9.

International Search Report and Written Opinion Corresponding to International Application No. PCT/US2013/049112; Date of Mailing: Dec. 13, 2013; 12 Pages.

International Search Report and Written Opinion Corresponding to International Application No. PCT/US2013/049247; Date of Mailing: Dec. 5, 2013; 13 Pages.

International Search Report and Written Opinion Corresponding to International Application No. PCT/US2013/040372; Date of Mailing: Jul. 16, 2013; 9 Pages.

International Search Report and Written Opinion Corresponding to International Application No. PCT/US2013/040379; Date of Mailing: Sep. 5, 2013; 14 Pages.

International Search Report and Written Opinion Corresponding to International Application No. PCT/US2013/040382; Date of Mailing: Dec. 6, 2013; 17 Pages.

Molecular Devices, Multi Dimensional Acquisition: Auto Focus Dialog, Molecular Devices Article #T20125, Aug. 27, 2009, Retrieved from the internet on Nov. 22, 2013 at URL http://support.meta.moleculardevices.com/docs/t20125.pdf.

Anderson et al. "Fresh cow mastitis monitoring on day 3 postpartum and its relationship to subsequent milk production", *Journal of Dairy Science*, Dec. 2010, vol. 93, No. 12, 5673-5683.

Ball et al. "An Antigen Capture ELISA Test using Monoclonal Antibodies for the Detection of Mycoplasma californicum in Milk", *Veterinary Immunology and Immunopathology*, 1990, vol. 25, 269-278.

Boothby et al. "Detecting Mycoplasma bovis in milk by enzyme-linked immunosorbent assay, using monoclonal antibodies", *American Journal of Veterinary Research*, 1986, 47(5):1082-1084.

Cimolai et al. "Culture-amplified Immunological Detection of *Mycoplasma pneumoniae* in Clinical Specimens", *Diagn Microbiol Infect Dis.*, 1988;9:207-212.

Fedorko et al. "Evaluation of a Rapid Enzyme Immunoassay System for Serologic Diagnosis of *Mycoplasma pneumoniae* Infection", *Diagn Microbiol Infect Dis.*, 1995;23:85-88.

(56) References Cited

OTHER PUBLICATIONS

Heller et al. "Antigen capture ELISA using a monoclonal antibody for the detection of *Mycoplasma bovis* in milk", *Veterinary Microbiology*, 1993, 37:127-133.
Kok et al. "Routine diagnosis of seven respiratory viruses and *Mycoplasma pneumoniae* by enzyme immunoassay", *Journal of Virological Methods*, 1994, 50:87-100.
Madsen et al. "The simultaneous direct detection of *Mycoplasma pneumoniae* and *Legionella pneumophila* antigens in sputum specimens by a monoclonal antibody immunoblot assay", *Journal of Immunological Methods*, 1987, 103:205-210.
Martinez et al. "Immunobinding Assay for Detection of *Mycoplasma bovis* in Milk", *Can J Vet Res*, 1990; 54:251-255.
Miettinen et al. Detection of *Mycoplasma hominis* Antigen in Clinical Specimens by Using a Four-Layer Modification of Enzyme Immunoassay (EIA), *Journal of Immunological Methods*, 1984, 69:267-275.
Talkington et al. "Analysis of Eight Commercial Enzyme Immunoassay Tests for Detection of Antibodies to *Mycoplasma pneumoniae* in Human Serum" *Clin. Diagn. Lab. Immunol.*, 2004, 11(5):862.
Tuuminen et al. "Improved sensitivity and specificity of enzyme immunoassays with P1-adhesin enriched antigen to detect acute *Mycoplasma pneumoniae* infection", *Journal of Microbiological Methods*, 2001, 44:27-37.
Uldum et al. "Enzyme Immunoassay for Detection of Immunoglobulin M (IgM) and IgG Antibodies to *Mycoplasma pneumoniae*", *Journal of Clinical Microbiology*, May 1992, vol. 30, No. 5, pp. 1198-1204.
European Examination Report for EP Application No. 13 724 126.1 mailed Feb. 24, 2016, 11 pages.

\* cited by examiner

RAPID DETECTION OF ANALYTES IN LIQUID SAMPLES

RELATED APPLICATIONS

This application claims the benefit of U.S. Provisional Patent Application Ser. No. 61/821,486, filed May 9, 2013, the disclosure of which is incorporated by reference herein in its entirety.

FIELD OF THE INVENTION

The present invention concerns methods and apparatus for detecting analytes, including pathogens such as *Mycoplasma* species, in liquid samples such as biological fluids.

BACKGROUND OF THE INVENTION

The *Mycoplasma* are a wide-spread group of bacteria. Species such as *M. pneumonia* and *M. genitalium* cause disease in humans. Related species cause disease in plants. *M. bovis* is considered one of the more pathogenic species and causes pneumonia, mastitis, and arthritis in cattle. In research laboratories, *Mycoplasma* species are frequent contaminants in cell cultures.

*Mycoplasma* are characterized by the absence of a cell wall. Unfortunately, the most important group of antibiotics, the beta-lactams (which include both the penicillins and the cephalosporins) function by inhibiting cell wall synthesis. With important antibiotics such as these unavailable for the treatment of *Mycoplasma* infections, there is a need for new and rapid methods and apparatus for the detection of these species so that they may be quickly detected on occurrence and controlled or eradicated before the spread thereof.

SUMMARY OF THE INVENTION

A first aspect of the invention is a device for detecting at least one analyte (and in some embodiments two, three, or four or more different analytes) in a liquid sample. The device generally comprises (i) a support having a chamber for receiving a biological fluid therein, wherein said chamber is an elongate chamber having a length axis; (ii) a (stationary or movable) carrier (in some embodiments in the form of an end cap, or connected to an end cap; in other embodiments in the form of an agitator in said elongate chamber). In some embodiments the carrier or agitator has opposite end portions and a side portion, with the carrier or agitator dimensioned to travel in said chamber along said length axis and/or permit the liquid sample to flow in the chamber therearound. In other embodiments (e.g., where the carrier is stationary, such as in the form of an end-cap or connected to an end cap), the carrier is positioned so that liquid in the chamber can be agitated there against, either (or both) thereby agitating the liquid sample; and (iii) at least one anti-analyte antibody coupled to either the carrier and/or the chamber side or end wall (e.g., coupled to a generally planar imaging surface, such as an interior surface of a carrier when the carrier is in the form of an end cap). In some embodiments, the carrier is or agitator is configured so as to bring analytes into sufficiently close physical proximity with their corresponding antibody to cause binding of the antibody to its corresponding analyte, thereby obviating the need to rely upon simple diffusion of analyte in the sample to the antibody for binding.

When a plurality of (e.g., two, three, four or more) different antibodies are bound to the carrier and/or chamber side wall, each of which binds a different analyte, they are preferably bound at separate and discrete locations on the carrier and/or chamber side wall portion.

A second aspect of the invention is a method of quantitatively or qualitatively detecting an analyte (or in some embodiments two or more different analytes) in a liquid sample. The method is carried out by (a) providing a device as described herein; (b) adding the liquid sample to the chamber; (c) agitating the support in the liquid sample within the chamber, or agitating the liquid against the support, sufficient to bind analyte in said liquid sample to the antibody (although in certain instances it may be preferable to hold the carrier stationary and move or agitate the liquid sample by stirring, rocking or the like); and then (d) detecting the presence or absence of binding of the one or more analytes to its respective antibody. Quantitative detection can be carried out by any suitable technique, such as manual or automated microscopy (e.g., fluorescence or epifluorescent microscopy) of cells or pathogens bound by the antibody.

Detection of analyte(s) bound to the respective antibodies may be carried out by any suitable technique, including but not limited to cell staining, immunoassay, radioassay, fluorescent assay, enzyme assay, ultraviolet illumination, optical microscopy, or the binding of suitable stains such as stains to the DNA or RNA within the cells to be detected (e.g., acridine orange), etc., including combinations thereof.

U.S. Pat. No. 5,776,710 to Levine et al. describes a method and apparatus for assaying analytes such as CD-4 cells, but generally relies on separation or concentration of cells by centrifugation, and is not adapted to the concurrent detection of multiple analytes.

While the present invention is concerned in one embodiment with the detection of *Mycoplasma*, it will be appreciated that the invention can also be applied to numerous additional analytes, as discussed further below.

Also described herein is a sample cartridge for microscopic imaging of a biological sample, the cartridge comprising: a body having an end portion and a pair of generally parallel opposing side edge portions, a locking edge portion formed on the body; a carrier removably connected to or permanently connected to the body; and at least one anti-analyte antibody coupled to either the carrier or to the chamber side wall portion (e.g., at the surface to be imaged, or supporting the sample to be imaged).

Also provided herein, for use when carriers as described above are in the form of a sample cartridge (that is, a form suitable for insertion onto a microscope stage), is an XYZ stage is for securing a sample cartridge in any suitable manual or automated microscope having X, Y, and Z planes of movement, the sample cartridge having an end portion, a pair of generally parallel opposing side edge portions, and a locking edge portion formed thereon. The XYZ stage comprises a base member having a planar stage surface portion; a pair of generally parallel oppositely facing guide members on said planar stage surface and configured for slideably receiving said cartridge therebetween; and a locking member on said planar stage surface portion and positioned to press against the sample cartridge locking edge portion when said sample cartridge is inserted between said guide members, so that pressure is exerted by said locking member through said sample cartridge against at least one of said guide members, whereby the cartridge is removably locked in place on the XYZ stage in the Z plane.

A further aspect of the invention is a method of automatically focusing a microscope on a specimen by capturing an image from each of a plurality of focal planes in or on said specimen, calculating a focus score for each of said images, selecting the focal plane corresponding to the image having the best focus score, and then repositioning said specimen relative to said microscope so that said microscope is focused on said selected focal plane, characterized by including a plurality of exogenous targets in or on said specimen.

A further aspect of the invention is an automated microscope comprising a specimen support stage, an objective lens, a camera, at least one drive assembly operatively associated with said support stage and/or said objective lens, and characterized by a controller operatively associated with said at least one drive assembly for carrying out an autofocus method as described herein.

Also described herein is a cartridge for imaging a specimen on an automated microscope, the cartridge comprising: a substrate, a chamber or generally planar imaging surface on or in the substrate for containing or supporting the specimen; a plurality of exogeneous targets in the chamber or on the surface; and (optionally but in some embodiments preferably) at least one optically transparent wall formed on or forming the chamber to facilitate imaging the contents thereof.

Also described herein is a method of detecting the presence of a pathogen, particularly a slow-growing pathogen such as *Mycoplasma* or *Mycobacteria* in a milk or colostrum sample, comprising: combining a milk sample with antibodies that bind *Mycoplasma*, said antibodies including IgY antibodies; and then detecting the presence or absence of binding of that pathogen to the antibodies.

The present invention is explained in greater detail in the drawings herein and the specification set forth below. The disclosures of all United States Patent references cited herein are to be incorporated by reference herein in their entirety.

DETAILED DESCRIPTION OF ILLUSTRATIVE EMBODIMENTS

Figure 1:
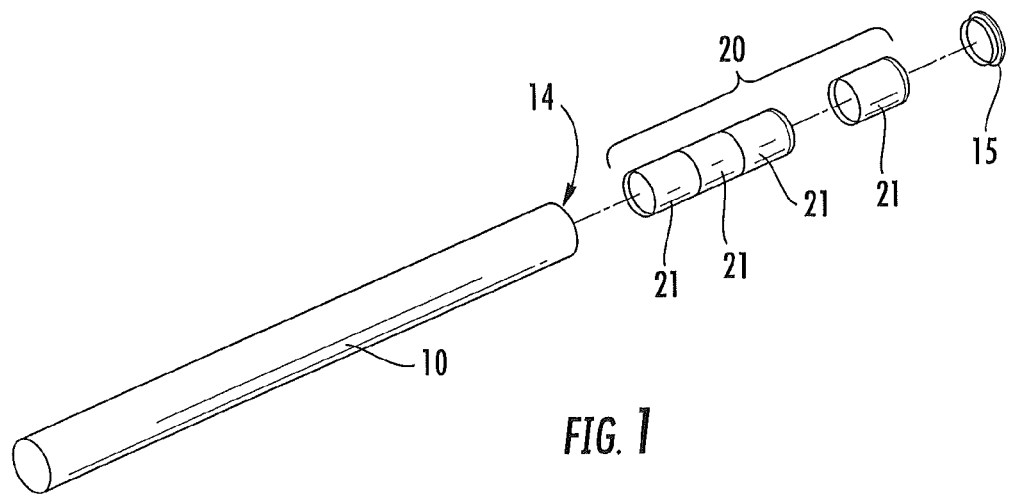
FIG. 1 is an exploded perspective view of a first embodiment of the invention.

The present invention now will be described more fully hereinafter with reference to the accompanying figures, in which embodiments of the invention are shown. This invention may, however, be embodied in many alternate forms and should not be construed as limited to the embodiments set forth herein. Like numbers refer to like elements throughout the description of the figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety.

Also as used herein, "and/or" refers to and encompasses any and all possible combinations of one or more of the associated listed items, as well as the lack of combinations when interpreted in the alternative ("or").

1. Definitions.

"Subject" as used herein includes both human and animal subjects for veterinary purposes, as well as plants for agricultural purposes. Examples of animal subjects include, but are not limited to, mammalian subjects such as dog, cat, cow, sheep, goat, horse, and pig subjects, fish such as salmon, trout, and tilapia, and avian subjects such as chicken, turkey, duck, geese, quail, and pheasant.

"Liquid sample" as used herein may be any liquid suspected of containing one or more analytes. The liquid sample is typically an aqueous sample, and may be provide as a single phase or multi-phase sample (e.g., an emulsion, dispersion, or suspension of solid or liquid particles in a (typically aqueous) continuous phase). For example: plant or animal tissue, or a solid food sample, may be homogenized in an aqueous solution to provide a liquid sample; a solid sample such as a soil sample may be rinsed in an aqueous rinse or wash solution such as water or buffer solution, and the rinse or wash solution used as the aqueous sample. A water sample may be taken from a pond, ocean, stream, river or the like, optionally diluted, and used as the liquid sample. In some embodiments, the liquid sample is a biological fluid. In some embodiments the liquid sample is a growth media such as cell or tissue culture media.

"Biological fluid" as used herein refers to a liquid solution or suspension comprising material collected from or excreted by a subject. Examples include, but are not limited to, milk, colostrum, secretions, whole blood, blood plasma, urine, mucus, lymph, throat and nasal swabs, sputum, bronchial lavage fluid, etc., from human and animal subjects; sap, nectar or juice from plants, tissue homogenates of, any thereof, and fractions of any thereof such as blood plasma. The fluid may be taken from a vector such as an insect that carries the pathogen, or may comprise a tissue homogenate of such vector. The biological fluid may further comprise or contain one or more additives such as washes, rinses, and/or other diluents (e.g., aqueous diluents such as saline solutions) in any suitable volume ratio of diluents to biological fluid (e.g., from 4:1, 3:1, 2:1, or 1:1 to 1:2, 1:2, 1:3, 1:4, etc.), along with other additives such as anticoagulants, preservative, salts, buffers, etc. The biological fluid is optionally but preferably complete or whole (e.g., whole milk or whole colostrum), which has not been subjected to separation steps such as filtering, fractioning, centrifuging, chromatography, etc.

"Milk" as used herein generally refers to mammalian milk of any species (e.g., cow, goat, human, etc.). The milk may be raw or pasteurized, depending upon the particular purpose of the test. Milk may be whole milk, low-fat or reduced fat milk, or skim milk. Milk may optionally be diluted (typically with an aqueous diluent such as distilled water, saline solution, or buffer solution), as discussed above.

"Colostrum" as used herein is a form of milk produced by mammals in the first few days after birth, that may be higher in antibodies (for imparting passive immunity to offspring). The term "colostrum" as used herein includes "secretions" as described below.

"Secretions" (or "mammary gland secretions") as used herein is a form of milk produced by mammals just prior to giving birth. Such secretions are sometimes also referred to as "colostrum" but in the present application "secretions" refers to the type of milk produced prior to the subject giving birth, while colostrum refers to the type of milk produced just after the subject giving birth.

"Analyte" (also referred to as "measurands") as used herein includes any suitable target of analysis or target of measurement. Such analytes, measurands, or targets as used herein may be any suitable compound or cell to which an antibody will bind, including but not limited to proteins, peptides, nucleic acids, toxins, and pathogens. "Toxin" as used herein includes, but is not limited to, mycotoxins and bacterial toxins (e.g., exotoxins, enterotoxins, and/or endotoxins).

"Mycotoxin" as used herein includes, but is not limited to, aflatoxins (e.g., aflatoxin B1, B2, G1, and G2), vomitoxin, ochratoxins (e.g., ochratoxin A, B, and C), citrinin, ergot alkaloids, and fusarium toxins (e.g., fumonisins, and trichothecenes).

"Enterotoxin" as used herein includes, but is not limited to, *Staphylococcus aureus* enterotoxin and *Escherichia coli* enterotoxin.

"Pathogen" as used herein may be any pathogen, including viral, fungal (including yeast), bacterial (including Gram negative and Gram positive bacteria), and protozoan pathogens. In some embodiments, the pathogen is a mollicute such as a *mycoplasma*.

"Mollicute" as used herein refers to a class of bacteria characterized by the absence of a cell wall. Orders within the class Molicutes include Acholeplasmatales, Anaeroplasmatales, Entomoplasmatales, Haloplasmatales, and Mycoplasmatales. Examples include, but are not limited to *Mycoplasma, Ureaplasma, Acholeplasma, Spiroplasma*, and *Phytoplasma*.

"Slow growing pathogen," as used herein, refers to microbial pathogens that require more than 10, 24 or in some embodiments 48 hours to double in population when grown in culture (as compared to, for example, bacteria such as *E. coli*, which can double in population in 2 to 3 hours). Examples of slow growing pathogens include, but are not limited to, *Borrelia, Pediococcus, Mycoplasma*, and *Mycobacteria*, See, e.g., PCT Application No. WO2002074991.

"*Mycoplasma*" as used herein refers to a genera of bacteria within the order Mycoplasmatales that lacking a cell wall. Examples include, but are not limited to, *mycoplasma bovis, mycoplasma genitalium, mycoplasma hominis, mycoplasma hyopneumoniae, mycoplasma laboratorium, mycoplasma ovipneumoniae, mycoplasma pneumonia, mycoplasma haemofelis, mycoplasma californicum*, etc.

"Mycobacteria" as used herein includes, but is not limited to, *Mycobacterium simiae, Mycobacterium bovis, Mycobacterium szulgai, Mycobacterium malmoense, Mycobacterium intracellulare, Mycobacterium avium, Mycobacterium gordonae, Mycobacterium africanum, Mycobacterium tuberculosis, Mycobacterium gastri, Mycobacterium marinum, Mycobacterium microti, Mycobacterium asiaticum, Mycobacterium scrofulaceum, Mycobacterium branderi, Mycobacterium paratuberculosis*, and *Mycobacterium kansasii*. See, e.g., European Patent Application No. EP1098003.

"*Borrelia*" as used herein includes, but is not limited to, *B. burgdoiferi, B. afzelii*, and *B. garinii* (the major species causing Lyme disease), along with other species such as *B. recurrentis, B. hermsii, B. parkeri, B. miyamotoi*, etc., which may cause borreliosis or relapsing fever borreliosis.

"Antibodies" as used herein refers to all types of immunoglobulins, including IgG, IgM, IgA, IgD, IgE, and IgY, and including combinations thereof. The antibodies may be monoclonal or polyclonal and may be of any species of origin, including (for example) mouse, rat, rabbit, horse, or human, avian (e.g., chicken) or reptile), or may be chimeric antibodies. See, e.g., W. Bergter et al., US Patent Application Publication No. 2004/0236076; M. Walker et al., *Molec. Immunol.* 26, 403-11 (1989). The antibodies may be recombinant monoclonal antibodies produced according to the methods disclosed in Reading U.S. Pat. No. 4,474,893, or Cabilly et al., U.S. Pat. No. 4,816,567. Antibody fragments included within the scope of the present invention include, for example, Fab, F(ab')2, and Fc fragments, and the corresponding fragments obtained from antibodies other than IgG. Such fragments can be produced by known techniques. Thus included are both truncated (yolk) IgY and complete or intact (plasma) IgY.

"Fluorescent stain" as used herein may be any suitable stain for fluorescence or epifluorscence microscopy, including but not limited to acridine orange, Astrazon Orange G (source: Sigma Aldrich), SYBR Green I (source: Life Technologies), SYTOX Green (source: Life Technologies), etc. Additional examples include but are not limited to those set forth in U.S. Pat. Nos. 7,638,290 and 7,236,236.

2. Antibodies and analytes for detection.

As noted above, the present invention may be utilized for detecting any of a variety of analytes to which antibodies may be raised, and to which antibodies bind. In some embodiments, the analyte is, or the analytes are, pathogens or toxins.

Numerous pathogens are known. See, e.g., U.S. Pat. No. 7,945,393. Examples of pathogens (e.g., human pathogens or those of animals or plants) that can be assessed using the methods described herein include bacteria (including eubacteria and archaebacteria), eukaryotic microorganisms (e.g., protozoa, fungi, yeasts, and molds) viruses, and biological toxins (e.g., bacterial or fungal toxins or plant lectins). Specific examples of such pathogens include protozoa of the genus *Cryptosporidium*, protozoa of the genus *Giardia*, bacteria of genera such as *Escherichia, Escherichia coli, Escherichia coli 157, Yersinia, Francisella, Brucella, Clostridium, Burkholderia, Chlamydia, Coxiella, Rickettsia, Vibrio, Leptospira, Enterococcus, Staphylococcus, Streptococcus*, methicillin-resistant *staphylococcus* (MRSA), *Enterobacter, Corynebacterium, Pseudomonas, Acinetobacter, Klebsiella*, and *Serratia*. Assessable organisms include at least *Escherichia coli, Yersinia pestis. Francisella tularensis, Clostridium perfringens, Burkholderia mallei, Burkholderia pseudomallei*, cryptosporidia microorganisms, Tularemia (*Francisella tularensis*), Brucellosis (*Brucella* species), *Chlamydia psittaci* (psittacosis), *Coxiella burneti* (Q fever), *Rickettsia prowazeki* (Typhus fever), *Vibrio vulnificus, Vibrio enteralyticus, Vibrio fischii, Vibrio cholera, Enterococcus faecalis, Staphylococcus epidermidis, Staphylococcus aureus, Enterobacter aerogenes, Corynebacterium diphtheriae, Pseudomonas aeruginosa, Acinetobacter calcoaceticus, Klebsiella pneumoniae, Serratia marcescens, Candida albicans, Microsporum audouini, Microsporum canis, Microsporum gypseum, Trichophyton mentagrophytes* var. *mentagrophytes, Trichophyton mentagrophytes* var. *interdigitale, Trichophyton rubrum, Trichophyton tonsurans, Trichophyton verrucosum*, and *Epidermophytum floccosum, Streptococcus* (including Strep A, B, C, G) filoviruses such as Ebola and Marburg viruses, naviruses such as Lassa fever and Machupo viruses, alphaviruses such as Venezuelan equine encephalitis, eastern equine encephalitis, and western equine encephalitis, rotaviruses, calciviruses such as Norwalk virus, and hepatitis (A, B, and C) viruses.

Additional examples of pathogens that can be detected by the methods and apparatus of the present invention include, but are not limited to, *Bacillus anthracis, Bartonella quintana, Brucella melitensis, Burkholderia mallei, Burkholderia pseudomallei, Chlamydia psittaci, Clostridium botulinum, Clostridium perfringens, Coxiella burnetti*, enterohemorrhagic *Escherichia coli, Francisella tularensis, Rickettsia mooseri, Rickettsia prowasecki, Rickettsia rickettsii, Rickettsia tsutsugamushii, Salmonella typhi, Salmonella, Shigella, Shigella dysenteriae, Vibrio cholerae, Yersinia pestis, Coccidioides immitis, Histoplasma capsulatum*, chikungunya virus, Congo-Crimean haemorrhagic fever virus, dengue fever virus, Eastern equine encephalitis virus, ebola virus, equine morbillivirus, hantaan virus, Japanese encephalitis virus, junin virus, lassa fever virus, Epstein Barr virus (infectious mononucleosis), lymphocytic choriomeningitis virus, machupo virus, marburg virus, monkey pox virus, Murray valley encephalitis virus, nipah virus, Omsk hemorrhagic fever virus, oropouche virus, Rift valley fever virus, Russian Spring-Summer encephalitis virus, smallpox virus, South American hemorrhagic fever viruses, St. Louis encephalitis virus, tick-borne encephalitis virus. Variola virus, Venezuelan equine encephalitis virus, Western equine encephalitis virus, white pox virus, yellow fever virus, botulinum toxins, *Clostridium perfringens* toxins, microcystins (Cyanginosins), Shiga toxin, verotoxin, Staphylococcal enterotoxin B, anatoxin A, conotoxins, palytoxin, saxitoxin, tetrodotoxin, stachybotrys toxins, aflatoxins, trichothecenes, satratoxin H, T-2 toxin, and ricin. Other examples include *Abrus precatorius* lectin, African swine fever virus, avian influenza virus, banana bunchy top virus, bluetongue virus, camelpox virus, cholera toxin, *Clostridium perfringens, Clostridium tetani, Cryptosporidium parvum, Deuterophoma tracheiphila, Entamoeba histolytica*, ergot alkaloids, *Escherichia coli* 0157, foot and mouth disease virus, *Giardia, Giardia lamblia*, goat pox virus, hendra virus, hepatitis A virus, hog cholera virus, human immunodeficiency virus, infectious conjunctivitis virus, influenza virus (including influenza A, influenza B, and influenza C viruses), Kyasanur Forest virus, *Legionella pneumophila*, louping ill virus, lyssaviruses, *Adenia digitata* lectin (modeccin), *Monilia rorei, Naegleria fowleri*, nipah virus, Murray Valley encephalitis virus, *Mycoplasma mycoides*, newcastle disease virus, oropouche virus, peste des petits ruminants virus, porcine enterovirus 9, powassan virus, pseudorabies virus, rinderpest virus, rocio virus, group B rotaviruses, *Salmonella paratyphi*, sheeppox virus, St. Louis encephalitis virus, substance P, *Serratia marcescens*, Teschen-Talfan virus, tetanus toxin, vesicular stomatitis virus, *Visctim album* lectin 1 (Viscumin), *Adena volkensii* lectin (volkensin), West Nile virus, *Xanthomonas campestris oryzae, Xylella fastidiosa*, and *Yersinia pseudotuberculosis*.

Examples of plant pathogens that can be assessed by the methods and apparatus of the present invention include, but are not limited to, *Burkholderia solanacearum*, citrus greening disease bacteria, *Erwinia amylovora, Xanthomonas albilineans, Xanthomonas axonopodis* pv. *citri, Bipolaris (Helminthosporium) maydis, Claviceps purpurea, Colletotrichum coffeanum virulans, Cochliobolus miyabeanus, Dothistroma pini, Fusarium oxysporum, Microcystis ulei, Neovossia indica, Peronospora hyoscyami, Puccinia erianthi, Puccinia graminis, Puccinia graminis* f. sp. *tritici, Puccinia striifonnis, Pyricularia grisea, Sclerotinia scierotiorum, Sclerotium rolfsii, Tilletia indica, Ustilago maydis, Phytophthora infestans*, and Fiji disease virus.

In some embodiments, the pathogen is detected directly. In other embodiments, the pathogen is indirectly detected by detecting the presence of a toxin which the antibody produces, whether or not the pathogen itself remains present.

Polyclonal antibodies used to carry out the present invention may be produced by immunizing a suitable animal (e.g., rabbit, goat, etc.) with an antigen (e.g., the analyte, optionally coupled to an adjuvant), collecting immune serum from the animal, and separating the polyclonal antibodies from the immune serum, in accordance with known procedures. Monoclonal antibodies used to carry out the present invention may be produced in a hybridoma cell line according to the technique of Kohler and Milstein, *Nature* 265, 495-97 (1975). For example, a solution containing the appropriate antigen may be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable media and the supernatant screened for monoclonal antibodies having the desired specificity. Monoclonal Fab fragments may be produced in *Escherichia coli* by recombinant techniques known to those skilled in the art. See, e.g., W. Huse, *Science* 246, 1275-81 (1989). Antibodies specific to the analyte may also be obtained by phage display techniques known in the art.

Once produced, the antibody is immobilized on a solid support in the appropriate region or location in the apparatus described below (e.g., on the carrier, on the chamber wall) in accordance with known techniques or variations thereof that will be apparent to those skilled in the art. See, e.g., U.S. Pat. Nos. 8,101,155; 8,043,821; 8,003,766; 7,829,294; 7,695,609; 7,288,253; and 7,247,453.

3. Apparatus.

Figure 2:
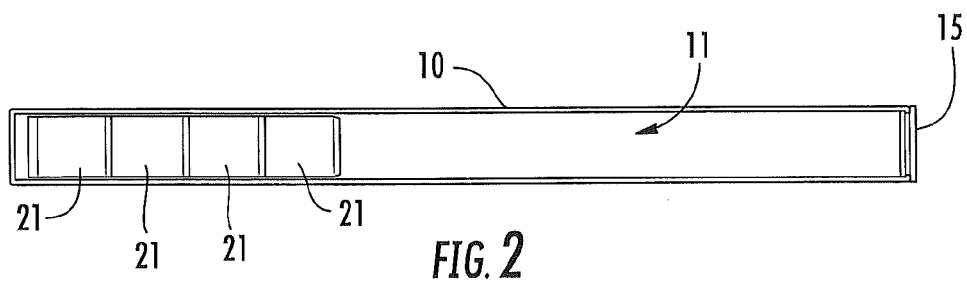
FIG. 2 is a side sectional view of the embodiment of FIG. 1.

As noted above, the present invention provides a device for detecting at least one analyte in a liquid sample. As illustrated in FIGS. 1-2, the device may generally comprise: (a) a support 10 having a chamber 11 or receiving a liquid sample therein, wherein said chamber is an elongate chamber having a length axis. A carrier or agitator 20 is disposed in the elongate chamber, the carrier having opposite end portions and a side portion, with carrier dimensioned to travel in the chamber along said length axis. At least one anti-analyte antibody is coupled to the carrier (e.g., at a side portion, end portion or internal pore, channel, or chamber), and/or to the chamber interior side wall portion. A port 14 is covered by a removable end cap 15 so that a liquid sample can be inserted into the chamber.

Figure 3:
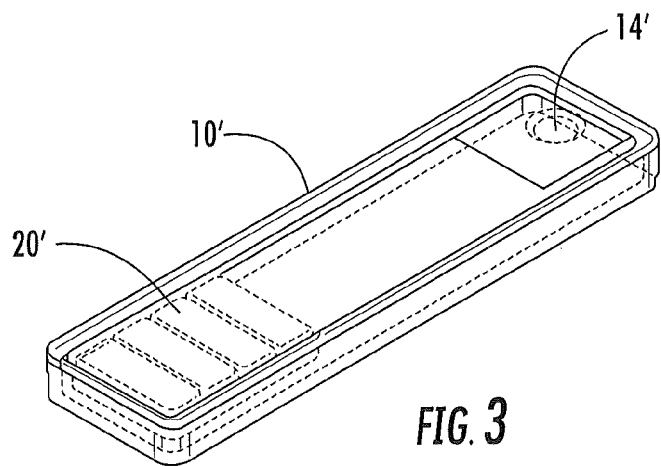
FIG. 3 is a perspective view of a second embodiment of the invention.
Figure 4:
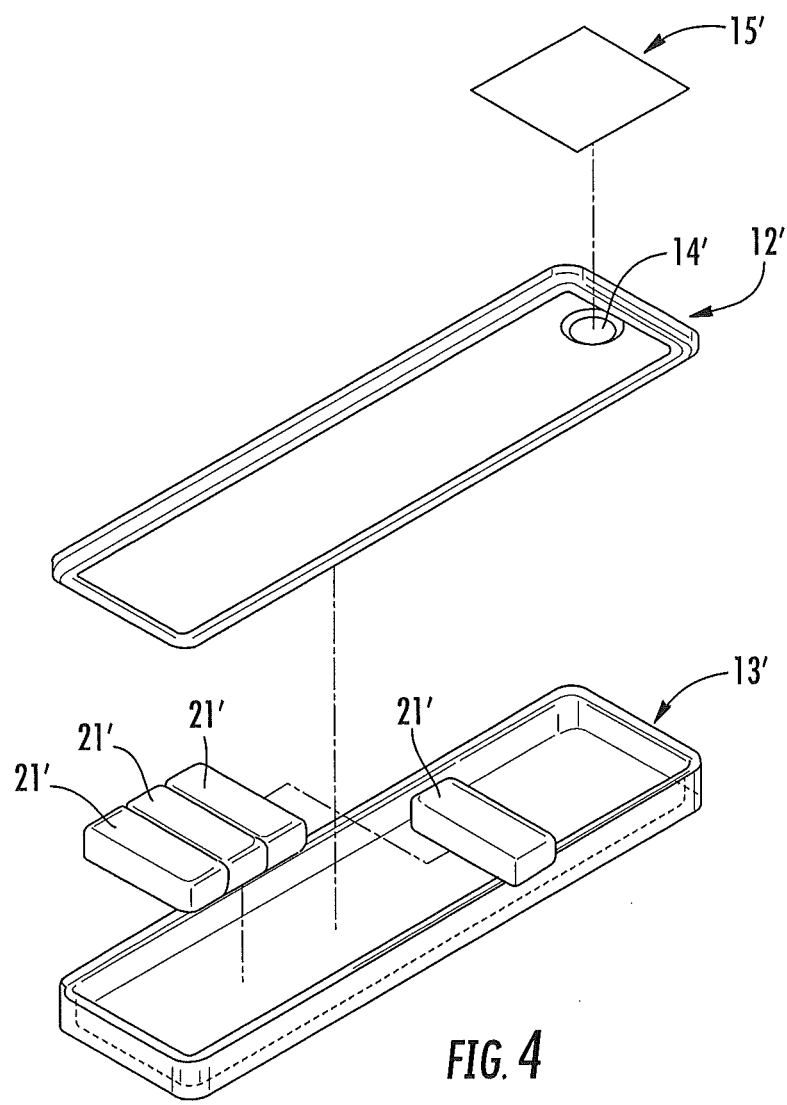
FIG. 4 is an exploded, perspective view of the embodiment of FIG. 3.
Figure 5:
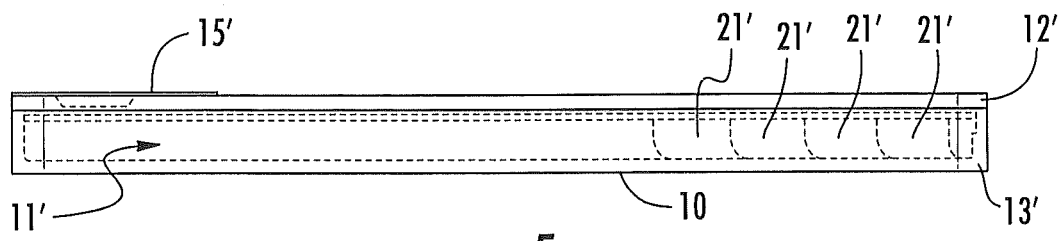
FIG. 5 is a side sectional view of the embodiment of FIG. 3.

In some embodiments, and as illustrated, the carrier 20 comprises a plurality of segments 21 connected coupled to one another, each of said segments having a side (or top) portion, with each of the side portions having a different antibody bound or coupled thereto, so that the presence of multiple different analytes in the liquid sample (e.g., four distinct analytes) may be detected An alternate, flat/planar, embodiment is shown in FIGS. 3-5, with like elements having like numbers assigned thereto. In this embodiment the segments may be areas on the same carrier. In this embodiment the support 10 ' defining chamber 11' is formed from an upper portion 12 ' and a lower portion 13'. The port 14' is formed in one end of the upper portion, and is sealed by an adhesive film 15'. The carrier 20' is again formed of a plurality of segments 21' connected to one another. When the support upper surface is optically transparent, this generally planar configuration is more suitable for quantitative determination of cellular analytes such as pathogens, which can then be detected/observed and counted by manual or automated microscopy.

The carrier or agitator may take any suitable form, including a round bead having antibody coupled to the entire surface thereof. However, as noted above, in some embodiments, the carrier or agitator 20, 20' comprises a plurality of segments 21, 21. In some embodiments, the plurality of segments comprises a pair of opposite end terminal segments and optionally at least one intermediate segment positioned therebetween, with each of said terminal segments fastened to intermediate segments by techniques such as heat staking, snap-fits, screw threads, etc.) In some embodiments, the carrier can further comprise an elongate core, with each of the plurality of segments having a transverse opening formed therein, and with each of said plurality of segments received on said core with said core extending through said transverse openings. In some embodiments, the carrier or agitator is magnetic, paramagnetic, or magnetizable (e.g., by inclusion of metal particles therein), to facilitate agitation as discussed further below. In some embodiments the carrier has a density greater than, or less than, the liquid sample for which the device is intended, so that the carrier or agitator sinks or floats in the liquid sample to facilitate agitation thereof.

Figure 6:
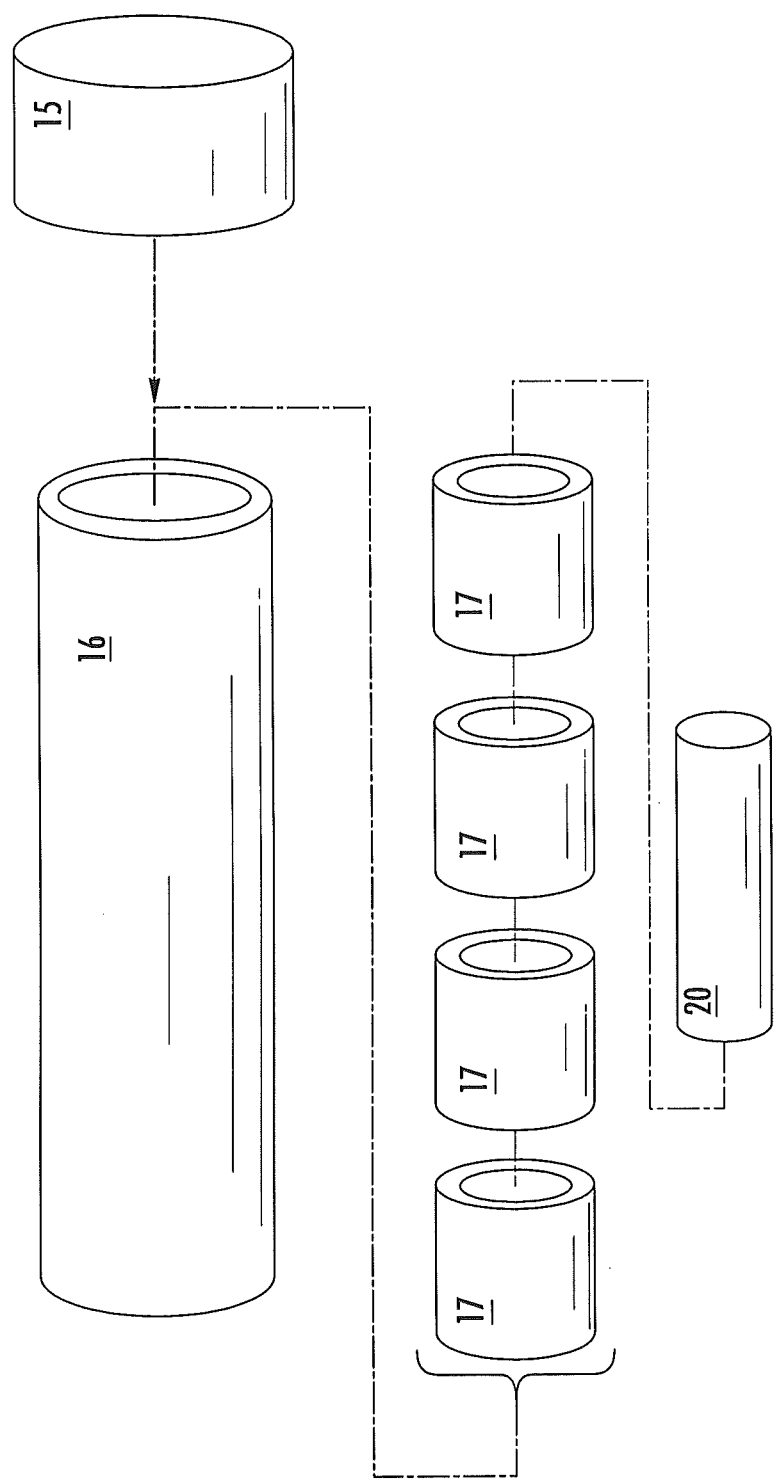
FIG. 6 is an exploded perspective view of a third embodiment of the invention.

In a still further embodiment illustrated in FIG. 6, the internal agitator is a single unitary part and does not carry any antibody. Instead, the chamber-forming support is provided as a plurality of chamber segments 16, which are nested together to form the internal chamber, through which the agitator 20 moves. As illustrated, the segments may be in the form of short cylinders (though it will be appreciated that other geometric forms, such as regular or irregular triangular, rectangular, pentagonal, etc., may also be utilized). Each segment 16 has an internal wall segment, to which different antibody may be bound. Spacer or "dummy" segments may optionally be provided. All of the segments may be disposed within an outer sleeve 17 to contain the liquid sample therein, with a cap 15 or other suitable sealing means such as an adhesive polymer film provided to contain liquid sample within the container.

In still another embodiment (not illustrated), the carrier or agitator is fixed, held, or restrained, by fastener or simply configuring the carrier to at least partially engage the chamber side wall, so that the carrier or agitator is substantially stationary in the chamber. Agitation of the liquid sample by the carrier or agitator is, in this embodiment, achieved by passing the liquid sample around the carrier.

In the foregoing, the support (or agitator) and/or the chamber may be transparent or opaque depending on the particular technique used to detect binding of the analyte to the antibody. In general, both the support and the chamber are composed of (but not limited to) an organic polymer, such as polystyrene or polycarbonate.

Figure 7:
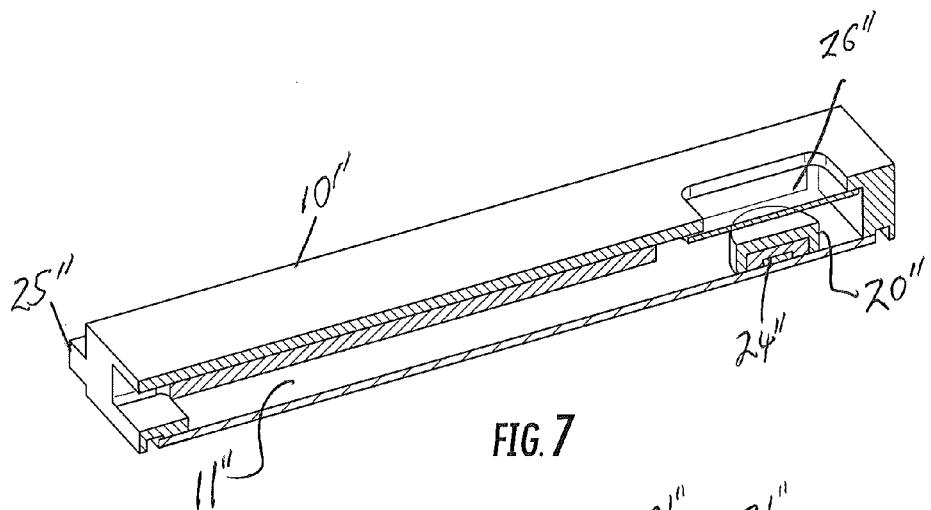
FIG. 7 is a side sectional perspective view of a fourth embodiment of the present invention.

FIG. 7 is a side sectional perspective view of a fourth embodiment of the present invention. Here the carrier 20" contains a magnet or ferromagnetic insert 24", which can be used to translate the carrier back and forth in chamber 11" through the use of a corresponding, external, magnetic or ferromagnetic element (not shown). The support 10" in this embodiment is in the form of a cartridge having generally parallel side edge portions 25", which can be conveniently inserted into the stage of a microscope. The support 10" has an optically transparent window 26" (e.g., formed from a polymer, coverslip, or other suitable material) through which captured analyte can be imaged (e.g., in a microscope as discussed further below). Alternatively, the entire support, or the entire upper portion or surface of the support, can be made from an optically transparent material. The support can be made as a single part or assembly of parts by any suitable technique, such as machined from a polymer, three-dimensionally printed, or molded.

The carrier, which in the non-limiting illustrative embodiment, is in the form of a "button," has an antibody coated reactive surface. While the carrier can be produced by any suitable technique, one suitable source is a Microfluor 2, black, flat-bottom microtiter plates (Thermo Scientific; part #7805), where the carrier is created from the microtiter plate by cutting the bottoms off of the individual microtiter plate wells and using the underside of thereof as the surface upon which to coat the anti-*Mycoplasma bovis* antibodies. This same technique may be used in many of the non-limiting examples shown below.

Figure 8:
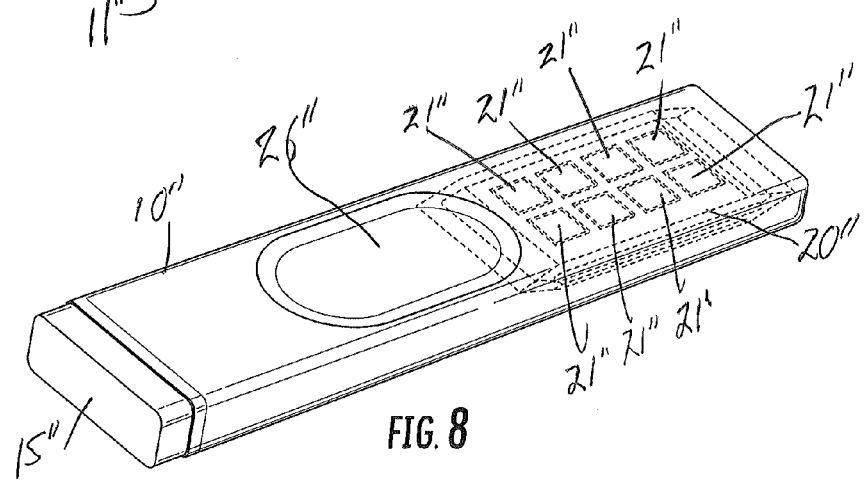
FIG. 8 is a perspective view of a fifth embodiment of the present invention.

FIG. 8 is a perspective view of a fifth embodiment of the present invention. Here the support 10" includes and end cap 15", an optically transparent upper surface or body portion, and the carrier 20" comprises multiple elements 21", all carrying a different antibody for capturing a different analyte. Agitation may be through rocking, etc., as described above.

Figure 9:
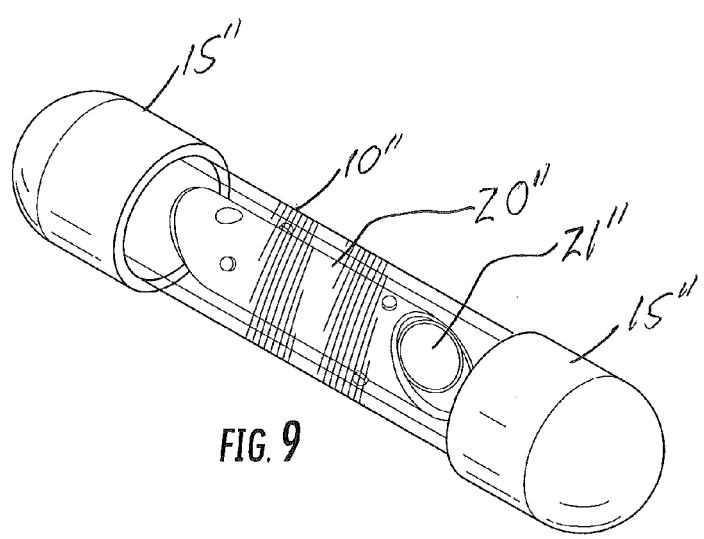
FIG. 9 is a side sectional view of a sixth embodiment of the present invention.
Figure 10:
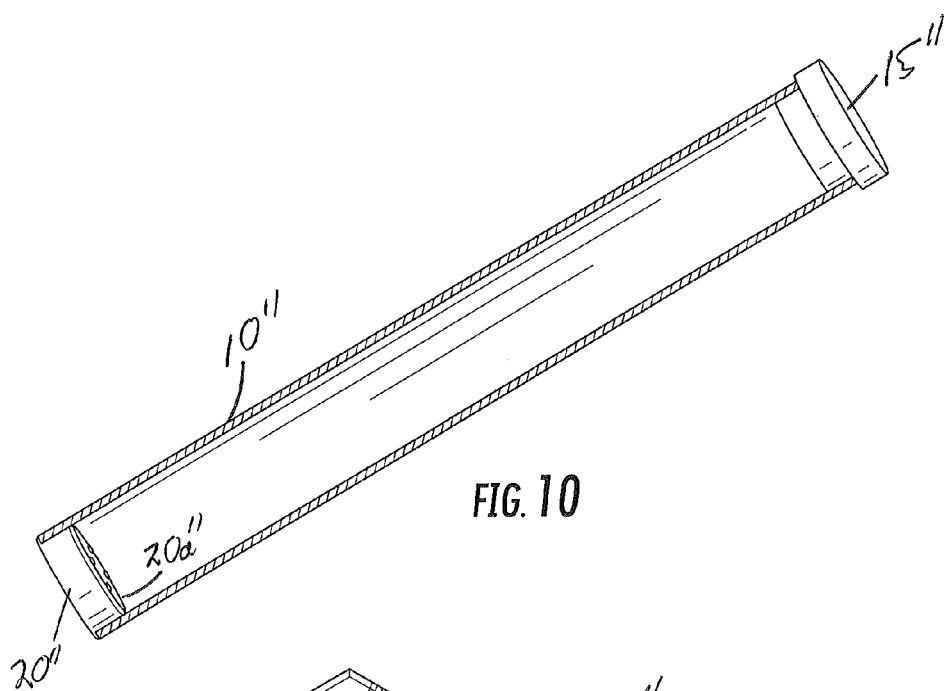
FIG. 10 is a side sectional view of a seventh embodiment of the invention, in which the carrier is a stationary and comprises a removable end cap of a vessel.
Figure 11:
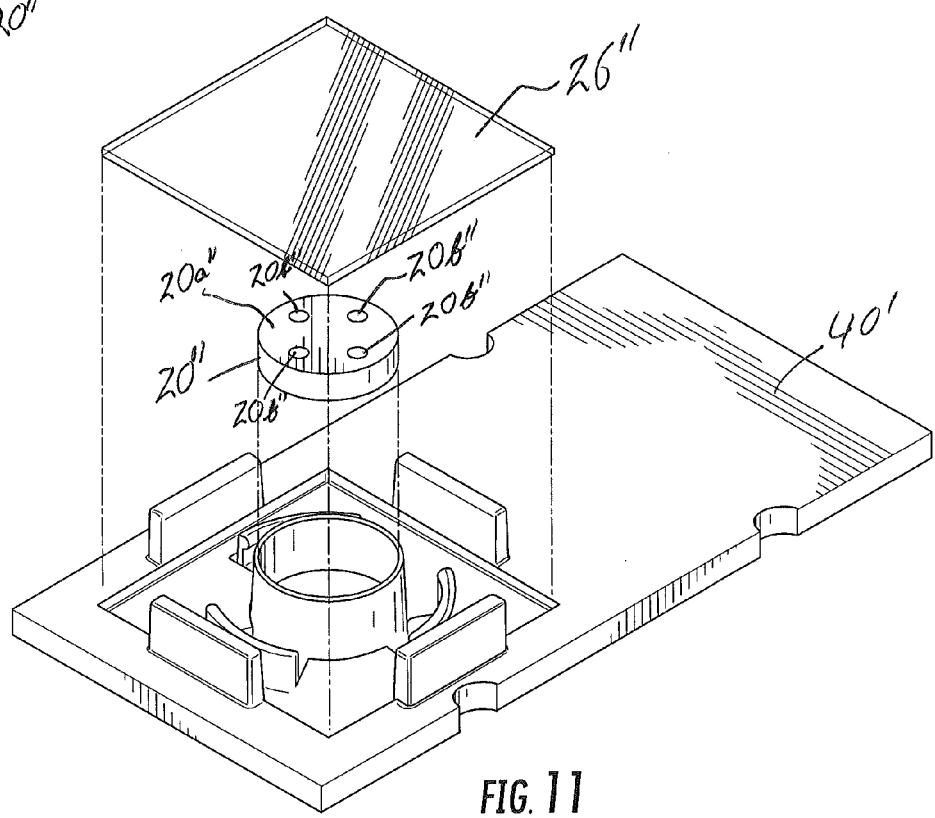
FIG. 11 is a perspective illustration showing how a carrier of the embodiment of FIG. 10 may be placed on a cartridge for imaging and detection.
Figure 12:
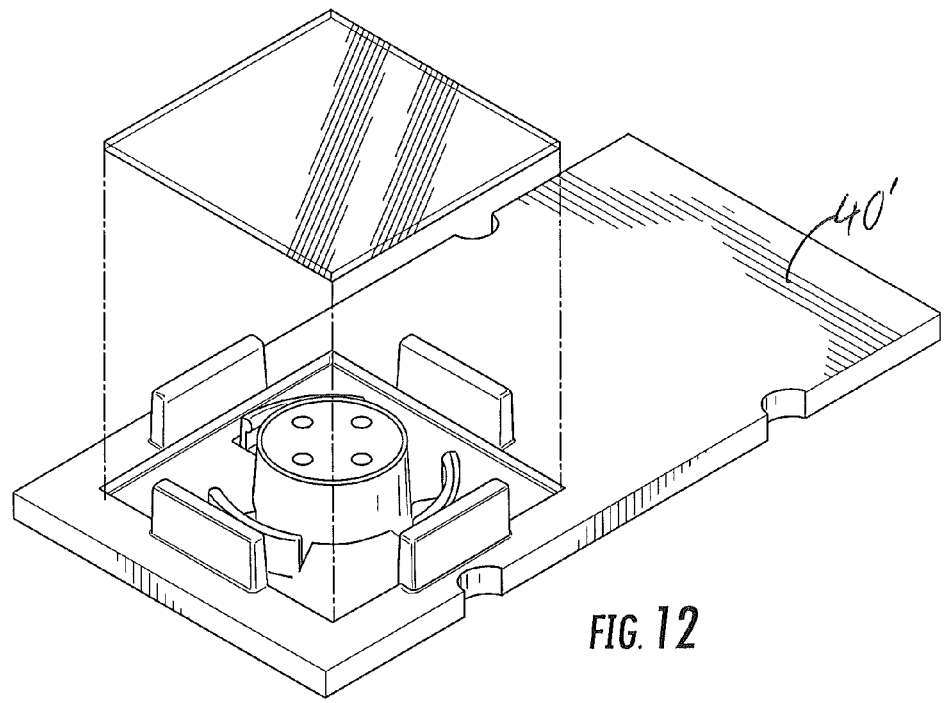
FIG. 12 is a perspective illustration similar to FIG. 11, with the carrier in place in the cartridge.
Figure 13:
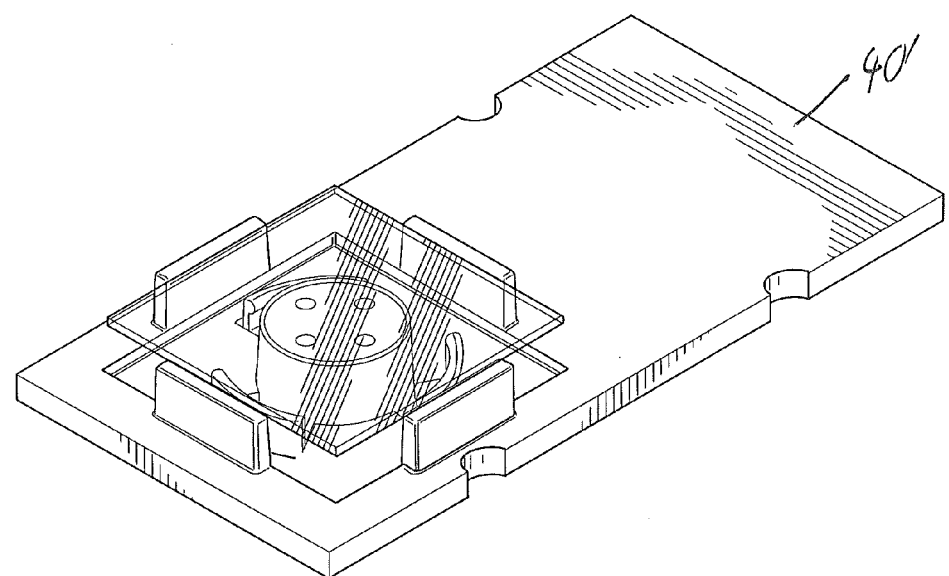
FIG. 13 is a perspective illustration similar to FIG. 11-12, with a cover slip placed on top of the carrier.

FIG. 9 is a side sectional view of a sixth embodiment of the present invention. Here the support 10" is formed from a glass tube, a pair of end caps 15" are formed from a flexible polymer material, and the carrier or agitator body 20 " is machined from stainless steel, into which carrier "button" segments 21" are inserted. Agitation may be through rocking, etc., as described above.

FIGS. 10 to 13 illustrate a seventh embodiment of the invention, comprising a support 10", an end cap 15" and a (now-stationary) carrier 20" in the form of a second removable end cap. The carrier has a substantially flat planar top surface 20a" that is coated with antibodies, and also includes a plurality of exogeneous targets such as focus beads at a plurality of locations 20b" thereon (shown as discrete locations, but the regions may be contiguous with one another, indeed the entire surface coated or carrying exogenous targets, so long as the targets provide multiple different focal points as discussed further below).

The embodiment of FIGS. 10-13 may be prepared from any suitable materials. For example, support 10" may be formed from an SSI Macro Pipet Tips, 5 ml; BioExpress; part #P3250-20, by scoring with a razor blade and then snapping off the bottom half of the tip such that the outside diameter of the tip at that cut end would fit inside the recessed area of the cap described below and provide a water-tight seal for that end of the vessel. The 'plug' end of a second Cap of the same type would then fit into the opposite end of the opening of the pipet tip and would provide a water-tight seal at that end. A cap may be a hollow top plug cap (LDPE), 12 mm; Stockwell Scientific; part #8565. The cap may be used to seal both ends of the reaction vessel as described above, and it also serves as a holder for the carrier. The cap may be formed into a carrier holder by cutting out the end of the cap in a size that matches the size of the carrier, and then snapping the carrier into the cut-out hole in the cap a water-tight seal is formed in the cap. The carrier is snapped into the cap with the orientation of the flat, antibody-coated reactive side of the Button facing inwards into the Reaction Vessel. The IgY is anti-*Mycoplasma bovis* antibody, IgY, produced by Ayes labs (Tigard, Oreg., USA) from *Mycoplasma bovis* antigen. Antibody (optionally also including polyclonal anti-*M. bovis* IgG antibody) may be coated onto the carrier by passive adsorption by overnight incubation at 4 degrees C. in accordance with known techniques, and as discussed further in the Examples below (numerous other materials and configurations may be used).

A liquid sample is then added to the chamber 11" (leaving sufficient empty volume or "head space" to permit agitation) and the chamber agitated by rocking, etc. as described further herein. After agitation, the carrier is removed and inserted in recessed well in cartridge 40'. A lip or rim may be provided around the circumference of the carrier, either formed on the carrier itself or by the well configuration, so that liquid is retained on the surface of the carrier when a cover slip is placed therein for insertion into a microscope XYZ stage for imaging, (for example, as discussed further below).

Figure 14:
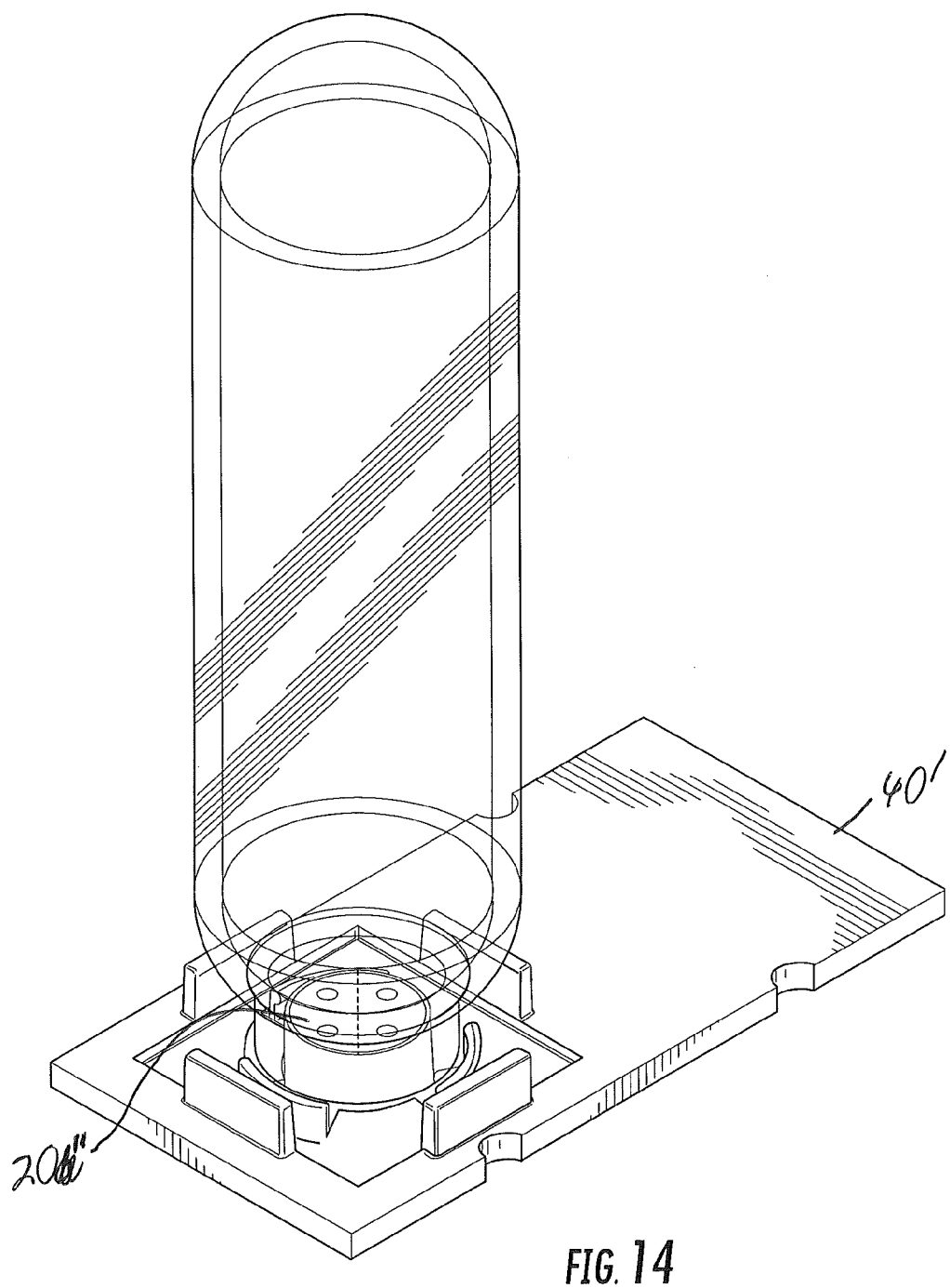
FIG. 14 is a perspective illustration of an eighth embodiment of the invention, where (in contrast to the embodiment of FIGS. 10-13) the carrier is fixed to the cartridge, and the vessel is removably connected to the cartridge above the carrier.
Figure 15:
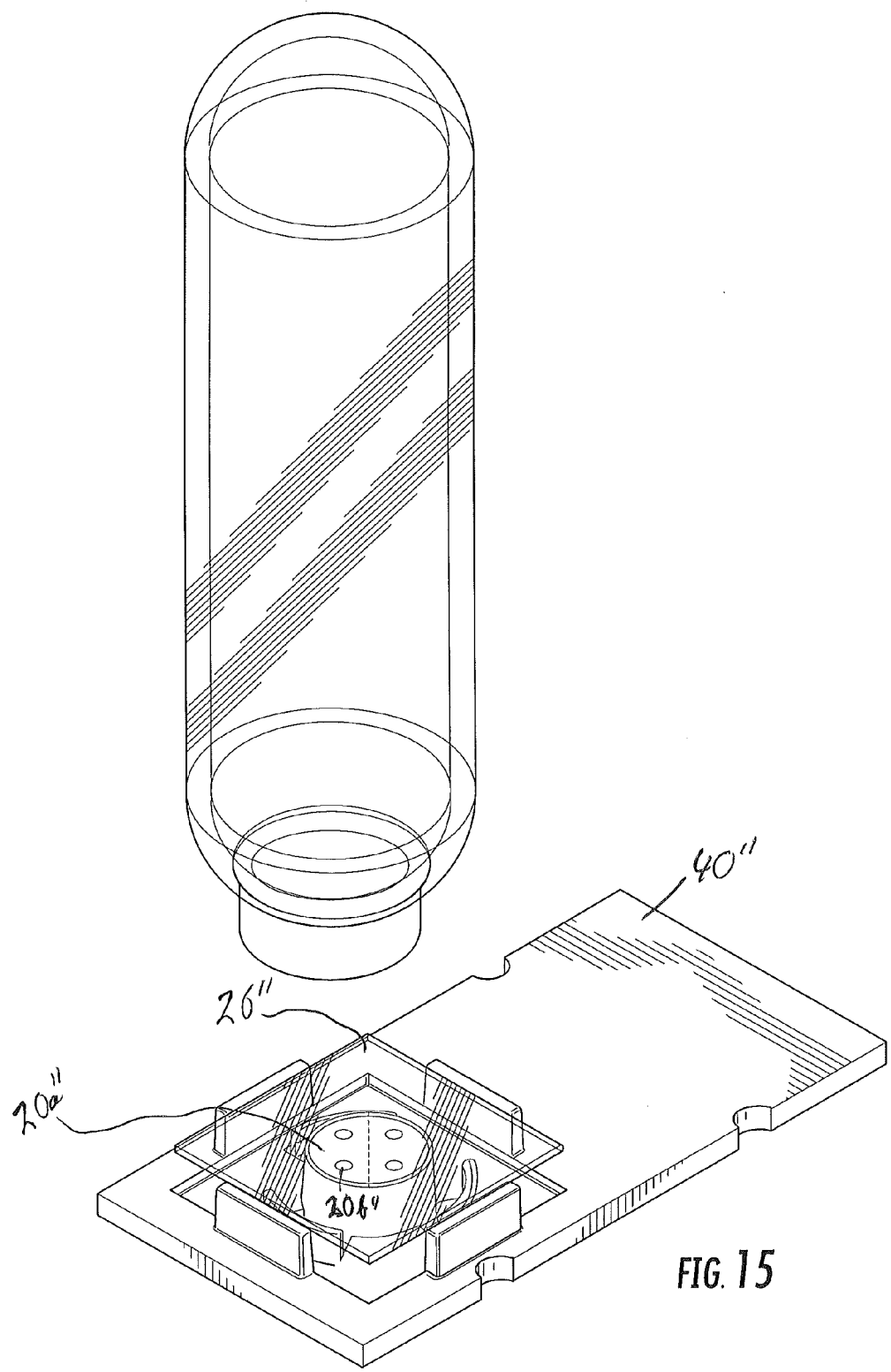
FIG. 15 is a perspective illustration of the embodiment of FIG. 14, with the vessel removed and a cover slip placed over the cartridge.

FIGS. 14 to 15 illustrate an eighth embodiment of the invention. This embodiment is similar to that of FIGS. 10-13 above, except that the carrier is fixed to the cartridge 40', and the support is in the form of a removable bottle or container which may be temporally fixed to the cartridge. This simplifies manipulation of the carrier by obviating the need to transfer the carrier from a support/sample container to a separate cartridge for imaging. The dashed line on the antibody carrier surface to be imaged represents regions where different antibodies may optionally be deposited, if it is desired to capture more than one analyte. Such a feature may be incorporated into any of the embodiments described above or below, or different antibodies may be provided on different carrier support segments as described above or below, or the two techniques for providing multiple antibodies to different analytes may be consolidated with one another.

Figure 16:
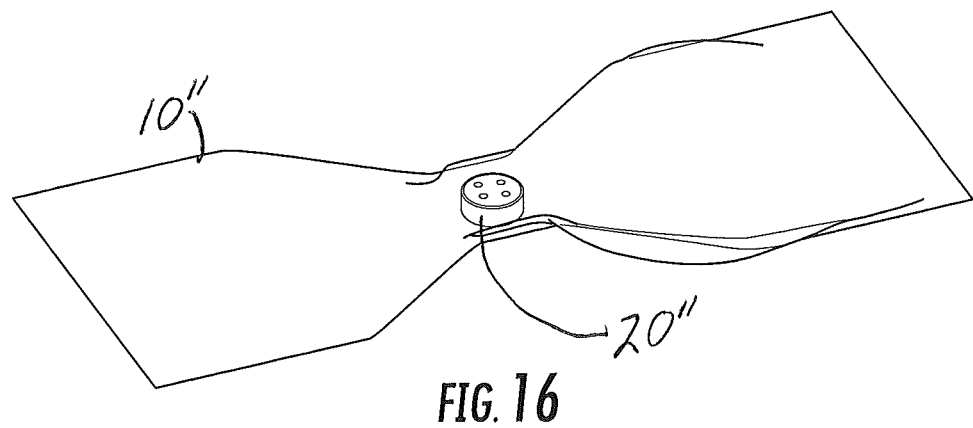
FIG. 16 is a perspective view of a still further embodiment of the invention, where the carrier is fixedly positioned in a flexible enclosure or "bag."
Figure 17:
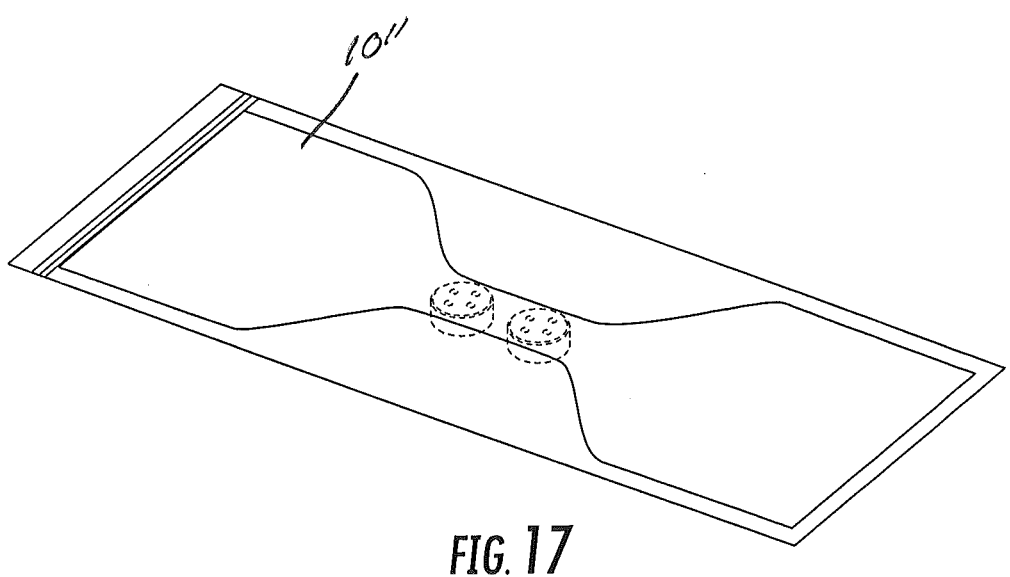
FIG. 17 is a perspective view of a still further embodiment, where a pair of carriers is fixedly positioned in a flexible enclosure.
Figure 18:
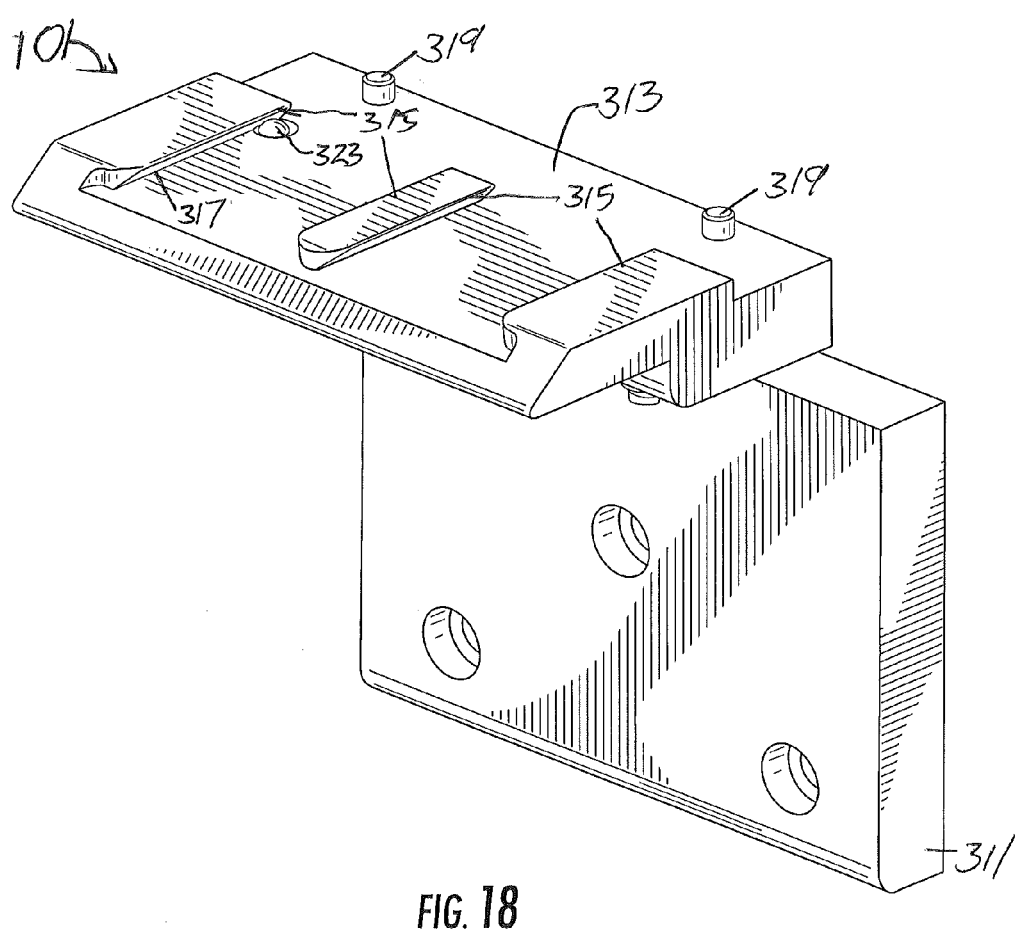
FIG. 18 is a perspective view of an XYZ stage for use in any suitable manual or automated microscope, as configured for retaining a pair of sample cartridges.
Figure 19:
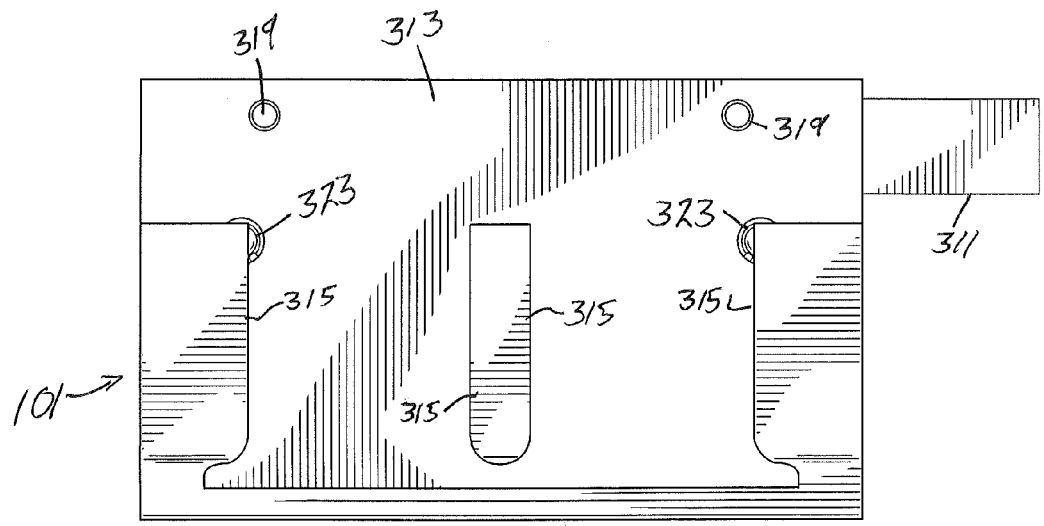
FIG. 19 is a top plan view of the XYZ stage of FIG. 11.
Figure 20:
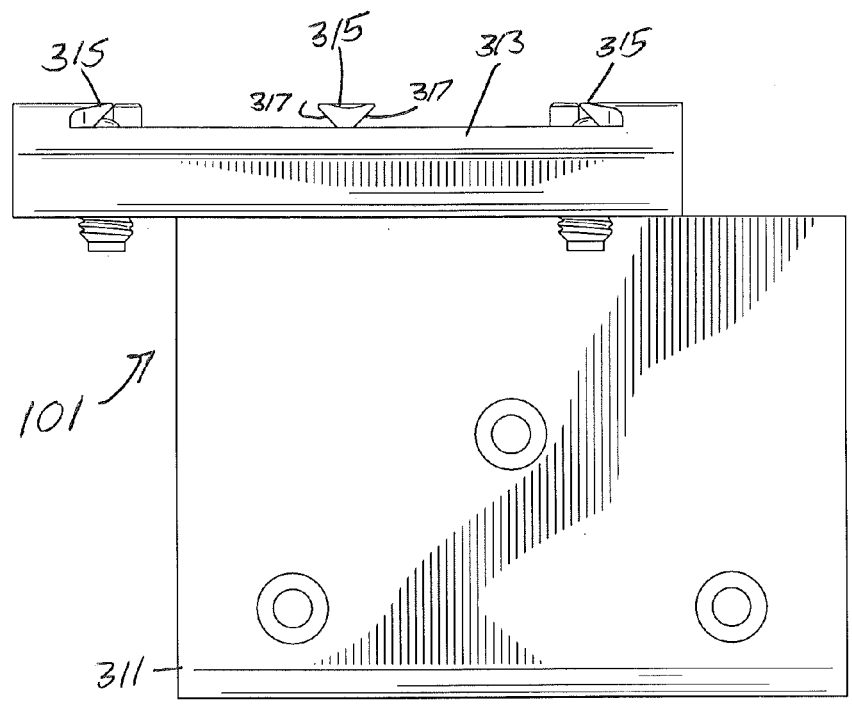
FIG. 20 is a side view of the XYZ stage of FIG. 11.
Figure 21:
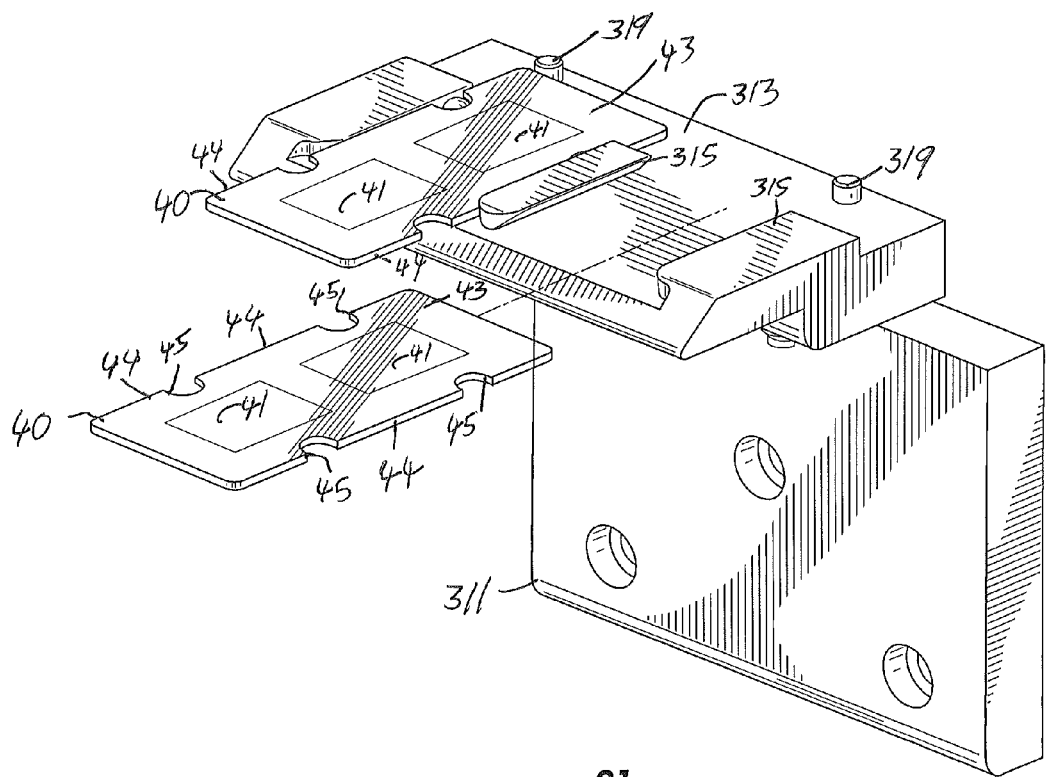
FIG. 21 is a perspective view of the XYZ stage of FIG. 11, showing a first sample cartridge seated in place, and a second sample cartridge to be inserted.

FIGS. 16 to 17 illustrate still further embodiments of the present invention. Here the support 10" comprises a flexible polymeric "bag" support (e.g., heat-sealable as shown in FIG. 16 or including a resealable closing element as shown in FIG. 17) in which one (FIG. 16) two (FIG. 17) or more (not shown) carriers are inserted. The support includes two enlarged end chambers and a constrained passage therebetween. The carriers may be formed of any suitable material, such as described above, and as above include exogeneous targets such as "focus beads" at four areas thereof. The carriers can be fixed within the constrained passage by any suitable means, such as an adhesive. The constrained passage is constrained relative to the volume of the chambers, which may be of the same relative diameter as the passage, but elongated to contain a larger volume than can be contained within the passage alone. The carriers may be dimensioned so that flow through the passages between the passage side wall and the carrier surface is as described above and below. Agitation may be achieved by reciprocally manually, or mechanically, expanding and compressing the respective chambers so that liquid therein flows back and forth over the one or more carriers.

As indicated above, any suitable antibody can be used to carry out the present invention, and coupling of the antibody to the carrier can be carried out in accordance with known techniques as noted above. Antibody affinity and amount are selected to achieve the desired level of sensitivity or detectable capture of pathogens, depending upon other variables such as agitation time and technique, as discussed further below.

In some embodiments, the at least one antibody comprises an anti-bacterial pathogen antibody; In some embodiments, the at least one antibody comprises an anti-*Mycoplasma* antibody; In some embodiments, the at least one antibody comprises an anti-*Staphylococcus aureus* antibody; In some embodiments, the at least one antibody comprises at least one antibody that binds to gram negative bacteria and at least one antibody that binds to gram positive bacteria.; In some embodiments, the at least one antibody comprises an antitoxin antibody; In some embodiments, one of said segments carries an anti-*Mycoplasma bovis* monoclonal antibody, and another of said segments carries an anti-*Staphylococcus aureus* monoclonal antibody; In some embodiments, two, three or four or more of the foregoing features are included in combination in the apparatus so that multiple different analytes are detected.

As noted, in some embodiments, the chamber has a length dimension and said carrier has a length dimension, wherein said chamber length dimension is at least twice (and preferably three or four times) that of said carrier length dimension In some embodiments, the chamber has a width dimension and said carrier has a width dimension, wherein said chamber width dimension is from 10 to 30 percent greater than said carrier width dimension In some embodiments, the chamber has a depth dimension and said carrier has thickness dimension, wherein said chamber depth dimension is from 10 to 30 percent greater than said carrier thickness dimension.

In some embodiments, the carrier and the chamber are configured so that said carrier cannot rotate in said chamber. In general, shapes that are irregular or nonspherical in cross-section may be used to achieve this result, including but not limited to triangular, rectangular, and other polygonal, compound, or irregular cross-sectional shapes.

In some embodiments, the chamber has a total volume of from 1 ml to 10 ml, and said carrier occupies from 20 to 40 percent of the chamber volume.

The space or distance between the carrier (specifically, carrier surfaces having antibody immobilized therein) and the chamber inner wall portion is, in some embodiments, so dimensioned as to achieve the desired level of contact of pathogens potentially carried by the biological fluid over the time period of the particular agitation procedure used. In some embodiments, the spacing or distance between these two surfaces is (on average) at least 20, 30 or 40 microns, up to 200, 300, or 400 microns. It will be appreciated that irregularities can be formed (such as lips, blocks, bumps, or other texture) can be formed on either or both surface portions as a way to enhance turbulence of the biological fluid during agitation to increase the probability of pathogen carried by the biological fluid being bound by antibodies immobilized on the carrier. In some embodiments, this geometry or configuration serves to insure or enhance the probability that the analyte(s) of interest will come sufficiently close to their corresponding antibody that they are specifically bound or "captured" thereby. For example, in the embodiments of FIGS. 1-6, when the carrier or agitator is driven by gravity (sinking, or floating, in the liquid sample) and the analytes are mycobacterial pathogens, the pressure differential that is created from the top of the carrier to the bottom of the carrier forces a liquid sample that contains very few pathogens and many other potential analytes that are not of interest up the space or annulus between carrier/agitator and the elongated chamber, very close to the antibody, increasing the probability of capture. For mycobacterial pathogens in milk, where the pathogens are potentially present in small numbers, or as a rare event (e.g., 100 mycoplasma organisms in a fluid containing millions of white cells and billions of fat globules), this feature is, in some embodiments, particularly important.

4. Methods Of Use

As noted above, methods of the invention are carried out by (a) providing a device as described herein; (b) adding the liquid sample to said chamber; (c) agitating the support in the liquid sample within the chamber sufficient to bind pathogen in said biological fluid to said anti-pathogen antibody; and then (d) detecting the presence or absence of binding of the pathogen to the antibody.

Agitation may be achieved by any suitable manual or automated technique that imparts motion of the carrier relative to the biological fluid, or vice versa. In contrast to the centrifugation used to concentrate and separate the carrier as described in U.S. Pat. No. 5,776,710 to Levine et al., agitation in the present invention is carried out in a manner which mixes or disperses the sample, and more particularly or mixes or disperses the analyte throughout the liquid s sample. The carrier may be moved by gravity (e.g., sink or float) as the chamber is repeatedly repositioned; the carrier may be held stationary while the chamber, and hence the fluid, is repositioned, and combinations thereof. Agitation is typically carried out at ambient or room temperature, and may be carried out for any suitable time. In some embodiments, agitation is carried out for a time of 10, 20 or 30 minutes, up to 1, 2 or 3 hours, or more.

In the alternative, as noted above, the carrier or agitator may be held, secured or positioned substantially stationary in the chamber (with constrained regions for flow of the liquid sample formed between the carrier and the chamber wall), and agitation of the liquid sample by the carrier or agitator achieved by reciprocally or continuously pumping, forcing, or flowing the liquid sample around and past the carrier (e.g., by application of a syringe, peristaltic pump, rolling chamber, gravity flow, shaking, or the like). The carrier or agitator forms constrained flow regions within the chamber that agitate by imparting shear forces and/or turbulence to the liquid sample, thus obviating the need for physically moving the carrier within the chamber when motion is imparted to the liquid sample by other means. As previously, in some embodiments the segments may be areas of the carrier.

In some embodiments, the carrier may be magnetic or comprise a paramagnetic material, so that agitation of the carrier can be carried out by application of a magnetic field. In other embodiments, agitation may be carried out by placing the device on a rocker, roller, shaker, or other suitable agitation device.

Those skilled in the art will be familiar with numerous specific quantitative and qualitative detection and assay formats and variations thereof which may be useful for carrying out the method disclosed herein. See generally E. Maggio, Enzyme-Immunoassay, (1980)(CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label." Applicants specifically intend that the disclosures of all U.S. Patent references cited herein be incorporated herein by reference in their entirety.

When the sample comprises cells to be imaged and/or counted, the cells may be stained by a suitable stain, including fluorescent stains such as acridine orange (see, e.g., U.S. Pat. No. 3,883,247).

In some embodiments, the methods and device achieve detectable capture of analytes such as *Mycoplasma bovis* or *Staphylococcus aureus* present in a biological fluid such as milk at a concentration of as little as $10^2$ pathogens per milliliter of biological fluid after one hour of agitation.

Exogeneous Targets.

General considerations for selecting the exogeneous target are as follows: The exogeneous target should be visible by the particular optical system in use. This will depend on the magnification, excitation wavelength, size of field of view, etc. This will influence decisions on which size, shape, emission wavlengths, etc. of the texture. In addition, the exogeneous target should be distinguishable from the target objects. Preferably, the The exogeneous target reside at substantially the same (or a known distance from) the focal plane of the target objects (e.g., be mixed with a biological sample suspected of containing cells to be imaged and/or counted, and/or placed in the same chamber as will contain a biological sample comprising cells to be imaged and/or counted). The exogeneous target should be of a size, shape, and number so as to not substantially obscure the view of the intended target objects, such as cells to be imaged and/or counted. And, the exogenous target should provide sufficient contrast with an empty field of view so as to provide an adequate focal peak and allow for reliable, reasonably rapid, and/or robust focusing.

The exogenous targets may be formed of any suitable material, including organic polymers, inorganic materials (including crystalline materials, amorphous materials, metals, etc.) and composites thereof.

The exogenous targets may be contained loosely within the chamber, fixed to one wall of the chamber, or surface to be imaged (e.g., by adhesive, by electrostatic, hydrophilic, or hydrophobic interaction, covalent bond directly or through a linking group, etc.), and/or formed on one wall of the chamber (e.g., by molding, etching, painting, silk-screening, lithography, etc.).

The exogenous targets may be opaque or transparent. When transparent the targets may be "tinted" so as to transmit light therethrough at a predetermined wavelength (for example, so that they appear red, green, blue, yellow, etc., to a human observer).

The exogenous targets may be regular or irregular in shape (for example, cylinders, spheres, cubes, pyramids, prisms, cones, rods, etc.). In some embodiments, the targets have an average diameter of from 0.1, 0.5 or 1 micrometers up to 2, 5, or 10 micrometers.

The number of exogenous targets is not critical, but in some embodiments the speed of the autofocus process can be increased by increasing, at least to a point, the number of exogenous targets in the chamber so that the targets are readily located in the automated microscope. Where a plurality of targets are included in the sample chamber (e.g., 2, 4, 6, 8 or 10 targets, up to 100, 200, 400, 600 or 800 exogenous targets, or more), in some embodiments that plurality preferably consists of or consists essentially of targets having substantially the same size, shape, and optical characteristics.

In some embodiments, the targets are beads, such as fluorescent microbeads. Such microbeads are commonly available and used for calibrating flow cytometers or fluorescent microscopes (see, e.g., U.S. Pat. Nos. 4,698,262; 4,714,682; and 4,868,126).

The targets are preferably optically distinguishable from cells to be counted (and hence would not be useful as calibration standards for the particular cells to be counted and/or imaged by the methods described herein). Optically distinguishable may be achieved by any suitable technique, such as by utilizing targets of a different and distinguishable shape from the cells to be counted, by utilizing targets that emit, transmit, and/or reflect light at a different wavelength from the cells to be counted when under the same illumination conditions, and combinations thereof.

6. Microscopes.

The present invention can be carried out with any suitable manual or automated microscope. Automated microscopes generally include a specimen support stage (e.g., configured for holding or securing a sample cartridge as described above), an objective lens, a camera operatively associated with the objective lens, at least one drive assembly operatively associated with said support stage and/or said objective lens. Examples of such microscopes include but are not limited to those described in U.S. Pat. Nos. 4,810,869; 5,483,055; 5,647,025; 5,790,710; 6,869,570; 7,141,773; and 8,014,583. In general, such apparatus includes a controller that is operatively associated with the camera and the at least one drive assembly which controller is configured through hardware and/or software to carry out an autofocus method as described herein (generally prior to acquisition of an image of the specimen or sample through the camera), typically through calculating a focus score. The focus score can be calculated by any suitable technique, including but not limited to those described in F. Groen et al., *A comparison of different focus functions for use in autofocus algorithms*, Cytometry 6, 81-91 (1985). Difference from the background, given a uniform background, can be calculated a number of ways, including but not limited to differences in contrast, gradient, and variance.

FIGS. 18 to 22 illustrate a first embodiment of an XYZ stage (101) that may be used in any suitable manual or automated microscope, as configured for retaining a pair of sample cartridges (40). As illustrated, each sample cartridge contains a pair of separate chambers (41), and the sample cartridges are reversibly insertable into the XYZ stage.

As shown in FIGS. 18 to 22, such a stage is configured to receive a sample cartridge having an end portion (43), a pair of generally parallel opposing side edge portions (44), and a locking edge portion formed (45) thereon, with each of said side edge portions having an upper corner portion, and with said locking edge portion positioned at an angle in relation to both said side portions and said front portion. While shown as part of a semi-spherical "notch" in a side edge portion of the illustrated embodiment (where the locking edge is a leading edge of the semi-spherical "notch"), the locking edge portion may be of any suitable shape, including curved, straight, and combinations thereof, and may be in any suitable position, including a top surface or bottom surface of the cartridge, so long as it is angled with reference to the front edge portion and/or opposite side edge portion in a manner that pressure is exerted thereagainst by the cartridge, as discussed below.

Figure 22:
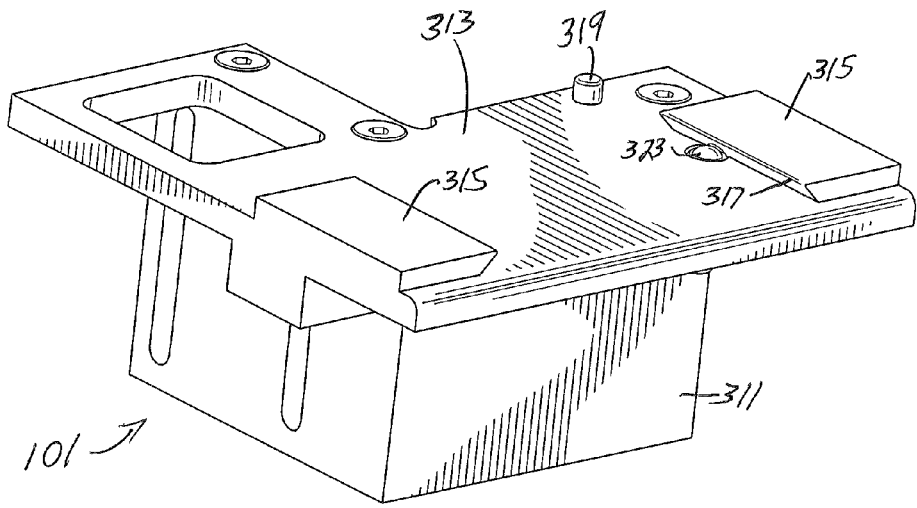
FIG. 22 is a perspective view of an alternate XYZ stage for an apparatus of FIG. 2, in which a single sample cartridge is to be inserted.

The XYZ stage itself comprises a base member (311) having a planar stage surface portion (313), and a pair of generally parallel oppositely facing guide members (315) on said planar stage surface, each of said guide members having an inwardly angled edge portion (317) configured for contacting one of the cartridge side edge upper corner portions when the sample cartridge is inserted therebetween. A terminal block member (319) is provided on the planar stage surface portion and positioned to contact the sample cartridge end portion when the sample cartridge is inserted between said guide members. A locking member (323) (e.g., a spring-loaded ball detent) is included on the planar stage surface portion and positioned to press against the sample cartridge locking edge portion when the sample cartridge is inserted between the guide members and in contact with said terminal block, so that pressure is exerted by said lock member through said sample cartridge against both said terminal block and one of said guide members, whereby the cartridge is removably locked in place on the XYZ stage in at least the Z plane of movement, preferably all three of the X, Y and Z planes of movement, and still more preferably with the cartridge secured with reference to, or with respect to, the X, Y, and Z axes of rotation as well. The embodiment of FIG. 22 is similar to the embodiments of FIGS. 18 to 21, except that it is configured to receive a single cartridge rather than a plurality of cartridges. The stage can be configured to receive any number of cartridges in any suitable shape or geometry as desired.

The present invention is explained in greater detail in the following non-limiting Examples.

EXAMPLE 1

Anti-Analyte Antibodies

Antibodies that bind to Aflatoxin are produced as described in J. Langone and H. Van Vunakis, J. Natl. Cancer Inst. 56, 591-595 (1976);, J. Groopman et al., *Proc. Natl. Acad. Sci. USA* 81, 7728-7731 (1984); G. Zhang and F. Chu, *Experientia* 45, 182-184 (1989), J. Gathumbi et al., *Lett. Appl. Microbiol* 32, 349-351 (2001), or variations thereof that will be apparent to those skilled in the art. In the alternative such antibodies are purchased from commercial sources such as Santa Cruz Biotechnology Inc., 2145 Delaware Avenue, Santa Cruz, Calif. 95060 USA.

Antibodies that bind to ergot alkaloids are produced as described in N. Hill et al., *Antibody binding of circulating ergot alkaloids in cattle grazing tall fescue*, Am. J. Vet. Res. 55, 419-424 (1994), or variations thereof that will be apparent to those skilled in the art.

Antibodies that bind to fumonisins are produced as desdribed in J. Azcona-Olivera et al., *Applied and Environmental Microbiology* 58, 169-173 (1992), or variations thereof that will be apparent to those skilled in the art.

Antibodies that bind to trichothecene mycotoxoin are produced as described in M. Abouzied et al., *Applied and Environmental Microbiology* 59, 1264-1268 (1993), or variations thereof that will be apparent to those skilled in the art.

Antibodies that bind *Staphylococcus aureus* enterotoxin are purchased from commercial sources such as Santa Cruz Biotechnology Inc., 2145 Delaware Avenue, Santa Cruz, Calif. 95060 USA.

Antibodies that bind *Staphylococcus aureus* cells are purchased from commercial sources such as Santa Cruz Biotechnology Inc., 2145 Delaware Avenue, Santa Cruz, Calif. 95060 USA.

EXAMPLE 2

Antibody Immobilization

Antibodies of the Examples above are coupled to a polystyrene carrier or carrier segment as described in the Figures herein, or to a polystyrene chamber side wall portion or segment thereof as described in the Figures herein, by physical adsorption as described in W. Qian et al., *Immobilization of antibodies on Ultraflat polystyrene surfaces*, Clinical Chemistry 46, 1459-1463 (2000), or variations thereof that will be apparent to those skilled in the art.

Antibodies of the Examples above are covalently coupled to a polystyrene carrier or carrier segment as described in the Figures herein, or to a polystyrene chamber side wall portion or segment thereof as described in the Figures herein, by the method described in O Siiman et al., *Covalently Bound Antibody on Polystyrene Latex Beads*, Journal of Colloid and Interface Science, 234, 44-58 (2001), or variations thereof that will be apparent to those skilled in the art.

Antibodies of the Examples above are coupled to a polycarbonate carrier or carrier segment as described in the Figures herein, or to a polycarbonate chamber side wall portion or segment thereof as described in the Figures herein, by the method described in R. Green et al., *Radioimmunoassay on Polycarbonate Membranes*, Appl. Microbiol 27, 475-479 (1974), or variations thereof that will be apparent to those skilled in the art.

Antibodies of the Examples above are coupled to a polycarbonate carrier or carrier segment as described in the Figures herein, or to a polycarbonate chamber side wall portion or segment thereof as described in the Figures herein, by the method described in P. Hajmabadi et al., *A method for Fabrication of Polycarbonate-Based Bioactive Platforms*, Journal of Laboratory Automation, 13, 284-288 (2008), or variations thereof that will be apparent to those skilled in the art.

EXAMPLE 3

Covalent Coupling of *Mycoplasma bovis* Mouse

Monoclonal Antibody to Carboxy Magnetic Particles

Preparation of Phosphate Buffer, 0.1 M, pH 5.0: Phosphate Buffer Powder 0.1 M (Sigma Aldrich cat #P7994, lot #041M6108, 4.3 grams) was dissolved in distilled water (250 ml) and the pH was adjusted to 5.0 by the addition of concentrated Hydrochloric Acid.

Preparation of Spherotech Carboxy Magnetic Particle Stock Solution: A tube was charged with 0.25 ml of Spherotech Carboxy Magnetic Particles (cat #CM-200-10, lot #AA01, 1.0% w/v, 21.4 microns, 10 ml). A magnet was applied to the bottom of the tube to pull the Carboxy Magnetic Particles to the bottom of the tube. The buffer was carefully pipetted off, the magnet removed, and the Carboxy Magnetic Particles were resuspended in 0.05 ml of Phosphate Buffer, 0.1 M, pH 5.0.

Preparation of N-(3-Dimethylaminopropyl)-N-Ethylcarbodiimide (EDC) Stock Solution: A tube was charged with N-(3-dimethylaminopropyl)-N-ethylcarbodiimide hydrochloride (Sigma-Aldrich, cat #E7750, lot #079K1395V, 10 mg) and dissolved in Phosphate Buffer, 0.1 M, pH 5.0 (50 µl).

*Mycoplasma bovis* (201) Antibody was purchased from Santa Cruz Biotechnology, Inc., Cat #sc-66067, lot #F1507, 100 µg/ml. This is a mouse monoclonal $IgG_1$ raised against *Mycoplasma bovis* cells.

Covalent Coupling of *Mycoplasma bovis* Mouse Monoclonal Antibody to Carboxy Magnetic Particles: A 1.7 ml tube was charged with Spherotech Carboxy Magnetic Particle stock solution (0.05 ml) and placed onto a magnetic separation rack for three minutes. At this point, the rust-colored Carboxy Magnetic Particles had collected on one spot on the wall of the tube. The supernatant was cautiously removed by pipette, taking care not to disturb the Carboxy Magnetic Particles that were magnetically stuck to the tube wall. The tube was removed from the rack and the Carboxy Magnetic Particles were re-suspended in 1 ml of Phosphate Buffer, 0.1 M, pH 5.0. The tube was placed onto a magnetic separation rack for three minutes. At this point, the rust-colored Carboxy Magnetic Particles had collected on one spot on the wall of the tube. The supernatant was cautiously removed by pipette, taking care not to disturb the Carboxy Magnetic Particles that were magnetically stuck to the tube wall.

The tube was charged with *Mycoplasma bovis* (201) Antibody (185 µl), and N-(3-dimethylaminopropyl)-N-ethylcarbodiimide (EDC) stock solution (19 µl). The tube was capped and placed in a rocker and rocked for two hours at room temperature. During the two hour rocking period the tube was removed and repeatedly inverted every 20 minutes to ensure thorough mixing of the reactants. Once the two hour rocking period was complete, the tube was placed onto a magnetic separation rack for three minutes. At this point, the cap was removed and the rust-colored Carboxy Magnetic Particles had collected on one spot on the wall of the tube. The supernatant was cautiously removed by pipette, taking care not to disturb the Carboxy Magnetic Particles that were magnetically stuck to the tube wall. The tube was removed from the rack and the Carboxy Magnetic Particles were suspended in Hyclone Dulbecco's Phosphate Buffered Saline (DPBS) Modified, without Calcium or Magnesium (Thermo Scientific, cat #SH30028.03, lot #AWH15873, 1 ml). The tube was placed onto a magnetic separation rack for three minutes. At this point, the Carboxy Magnetic Particles had collected on one spot on the wall of the tube. The supernatant was cautiously removed by pipette, taking care not to disturb the Carboxy Magnetic Particles that were magnetically stuck to the tube wall. The Carboxy Magnetic Particles were washed two more times with Hyclone Dulbecco's Phosphate Buffered Saline (DPBS) Modified, without Calcium or Magnesium (Thermo Scientific, cat #SH30028.03, lot #AWH15873, 1 ml).

The Carboxy Magnetic Particles were suspended in Hyclone Dulbecco's Phosphate Buffered Saline (DPBS) Modified, without Calcium or Magnesium (Thermo Scientific, cat #SH30028.03, lot #AWH15873) to bring them to a final concentration of 0.25% (w/v).

The Carboxy Magnetic Particles with *Mycoplasma bovis* Mouse Monoclonal Antibody covalently bound suspended in Hyclone Dulbecco's Phosphate Buffered Saline (DPBS) Modified without Calcium or Magnesium at a final concentration of 0.25% (w:v) is the stock solution used in the example below.

EXAMPLE 4

Capturing *Mycoplasma bovis* with *Mycoplasma bovis* Mouse

Monoclonal Antibody Covalently Bound to Carboxy Magnetic Particles

*Mycoplasma bovis* culture was prepared by growing *Mycoplasma bovis* anaerobically for 7 days at 37° C.

A sterile tube was charged with *Mycoplasma bovis* culture (100 µl) and Carboxy Magnetic Particles with *Mycoplasma bovis* Mouse Monoclonal Antibody covalently bound suspended in Hyclone Dulbecco's Phosphate Buffered Saline (DPBS) Modified without Calcium or Magnesium at a final concentration of 0.25% (w:v) (50 µl). The mixture was incubated for two hours, with agitation of the mixture every 15 min. Following incubation, the tube was placed onto a magnetic separation rack for three minutes. At this point, the Carboxy Magnetic Particles had collected on one spot on the wall of the tube. The supernatant was cautiously removed by pipette to remove unbound *Mycoplasma bovis* cells.

The tube was removed from the rack and the Carboxy Magnetic Particles were suspended in Hyclone Dulbecco's Phosphate Buffered Saline (DPBS) Modified, without Calcium or Magnesium (Thermo Scientific, cat #SH30028.03, lot #AWH15873, 1 ml). The tube was placed onto a magnetic separation rack for three minutes. At this point, the Carboxy Magnetic Particles had collected on one spot on the wall of the tube. The supernatant was cautiously removed by pipette, taking care not to disturb the Carboxy Magnetic Particles that were magnetically stuck to the tube wall. This washing procedure was repeated twice.

The Carboxy Magnetic Particles with *Mycoplasma bovis* attached were resuspended in Hyclone Dulbecco's Phosphate Buffered Saline (DPBS) Modified, without Calcium or Magnesium (Thermo Scientific, cat #SH30028.03, lot #AWH15873, 50 µl). A 10 µl aliquot of the 50 µl Carboxy Magnetic Particles suspension was combined in a tube with a 0.01% Acridine Orange, pH=3.0, (10 µl) solution for staining. After incubation for 10 minutes at room temperature, 10 µl of the staining mixture was loaded onto one a flat view cell and the view cell was read under a Zeiss fluorescent microscope. *Mycoplasma bovis* organisms were observed on the surface of the beads, confirming capture thereof.

EXAMPLE 5

Stationary Carrier with Polyclonal IgG/IgY Combination

Carriers are passively coated overnight at 4° C. with a polyclonal IgG/IgY combination (Chicken/Rabbit) a *Mycoplasma bovis*, then post-coated with PBS containing Blocker (commercial reagent, PBS-Superblock (source: Thermo-Scientific). for 2 hours at ambient temperature, and then washed 3 times with $PBST_{w20}$. The carriers may then be stored in PBS containing 0.1% Blocker and 0.05% Azide at 4° C.

The reaction vessel is then assembled by "snapping" the coated carrier onto the bottom of the reaction vessel without any further manipulation.

Two 2 ml testing matrix (i.e. milk) is then added, after which 2 ml 2×PBS+2× non-lysing/fat miscible detergent is added, to a final concentration of 0.25/0.5% detergent.

Acridine Orange (AO) is added to a final concentration of 0.05%. Reaction vessels are then gyrated at 3 RPM for 4 hours at 37° C. in an invertible mixer to mix the contents. Following this mixing step, the carrier is then washed with 1×PBS+ non-lysing Detergent containing 0.0005% Acridine Orange, and then washed further with $PBST_{w20}$ containing 0.0005% Acridine Orange.

After washing, the carrier is removed from the vessel and placed on a suitable holder for mounting on a microscope stage. 2.0 ul $PBST_{w20}$ containing 0.0005% Acridine Orange is then added to the surface of the carrier, the carrier covered, with a number 2 microscope cover slip, and imaged with a fluorescent microscope. Cells bound to the IgG/IgY will appear as "green apple" points of light at 20-40× magnification.

EXAMPLE 6

Exogenous Target-Assisted Autofocus

An embodiment of the invention is carried out by addition of microscopic fluorescent beads to a sample to be imaged, in combination with an automated microscope including an XYZ stage under the control of a computer. A sufficient concentration of such beads will ensure that there is a very high probability of having beads within any given field of view, thereby ensuring that there is sufficient texture for the autofocus algorithm.

In general, when an automated microscope focuses, a typical approach is a sequence as follows:
1. Move to some Z location.
2. Mathematically process the digital image to obtain a "score" of the image that represents, in relative terms, whether the field of view is in focus.
3. Repeat steps 1 and 2 until a peak is found in the focus graph. This peak will represent the position at which that field of view is in best focus.

Figure 23:
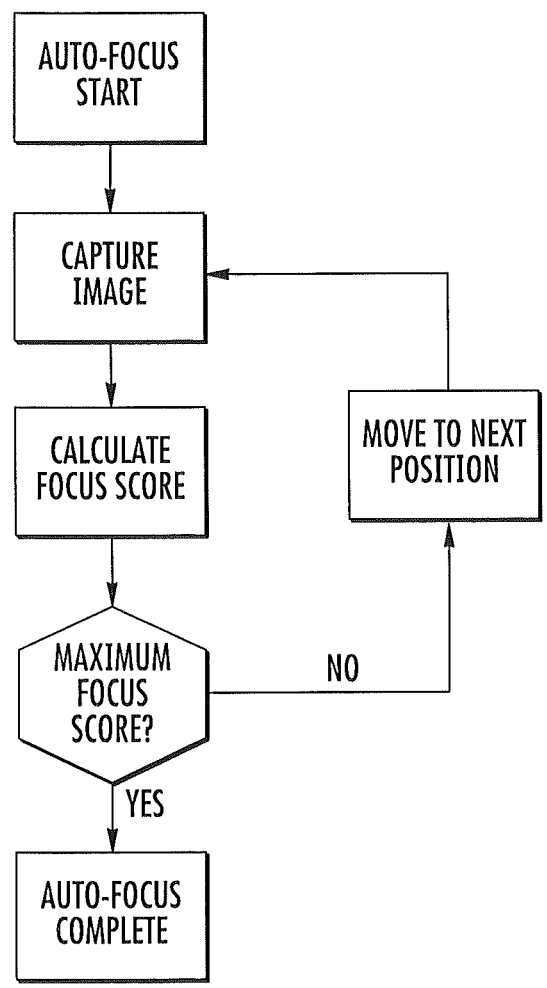
FIG. 23 illustrates an autofocus protocol for use in carrying out the present invention.

This sequence is schematically illustrated in FIG. 23 herein.

Figure 24:
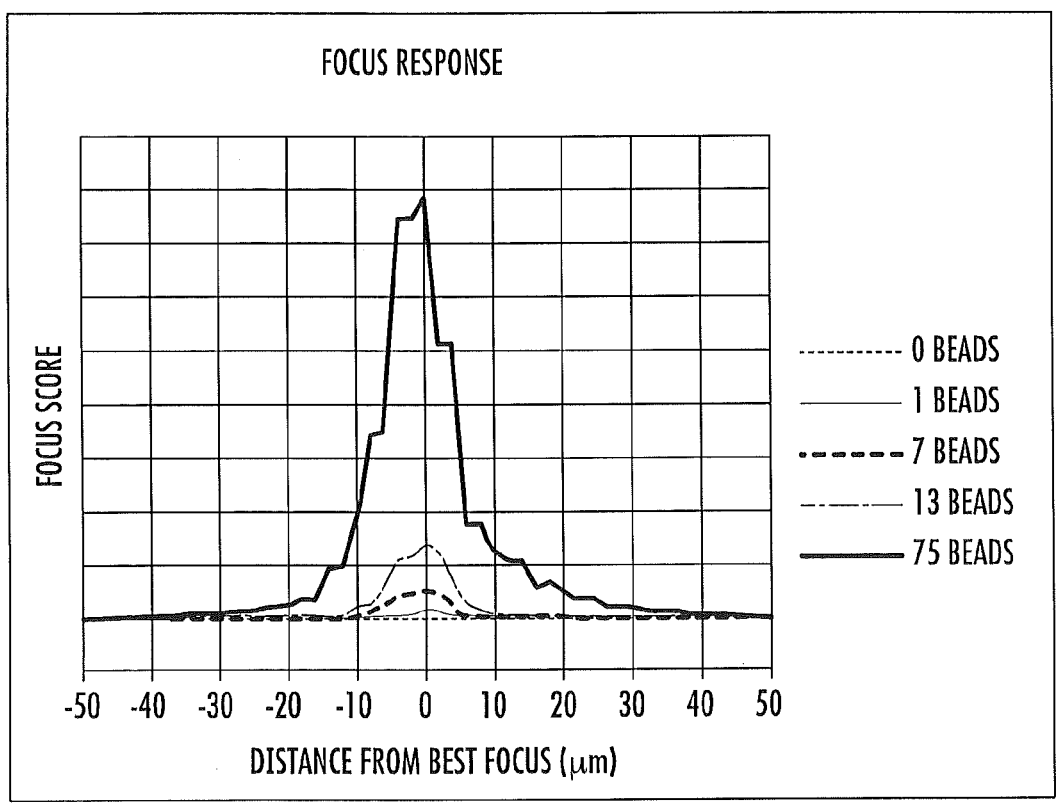
FIG. 24 illustrates results with fluorescent beads in an autofocus protocol.

FIG. 24 shows the response of the focus score, as a function of Z position, for a number of different fields of view, where various numbers of fluorescent microbeads are added to the field of view as exogenous targets. If there is nothing in the field of view, then it is numerically impossible to distinguish the "actual" in-focus position from any other image. The data is dominated by noise. With the addition of one bead to the field of view, a slight maximum is found at the position of best focus. With subsequently more and more addition of texture (more and more beads in the field of view), the focus peak becomes stronger and stronger. This is a numerical representation of the idea that the more exogenous targets exist within a field of view, the "easier" it is to focus (allows for larger Z steps, fewer opportunities to find false peaks, etc.).

EXAMPLE 7

Sample or Surface Interpolation

By including exogeneous focal targets at a plurality of separate locations in the sample to be imaged, or on the sample carrier surface to be imaged (so long as cells/analytes to be imaged and focus particles are in the same image plane or "Z stack"), the surface or sample can be interpolated by inclusion of a suitable interpolation program, routine or subroutine within the autofocus subroutine, to thereby facilitate imaging of the sample, or speed imaging of the sample.

Such interpolation can be carried out by any suitable algorithm or method, including but not limited to the planar best fit method, the weighted least squares fit method, and the quadratic fit method. Such procedures are known and described in, for example, I. Coope, "Circle fitting by linear and nonlinear least squares". *Journal of Optimization Theory and Applications* 76 (2): 381 (1993); Ake Bjorck, *Numerical Methods for Least Squares Problems*, Society for Industrial and Applied Mathematics (April 1996); etc.

The planar best fit method is illustrated by the equation:

$$z = Ax + By + C$$

Method 1 involves the average of x, y and z points; Method 2: Least Squares Linear Regression; and Method 3: Weighted Least Squares Regression. Data: x, y, and z focus points collected outside the viewing/imaging sample area. At least 3 data points are required.

The quadratic fit method is illustrated by the equation:

$$z = Ax^2 + By^2 + Cxy + Dx + Ey + F.$$

The method involves a second order quadratic surface. Data: x, y, and z focus points are collected somewhere outside the viewing/imaging/sample area. At least six data points are required.

When the cells to be imaged are collected and imaged within the same enclosed chamber, the exogeneous targets may be simply included in the chamber. When cells to be imaged are captured by antibodies bound to a carrier surface, the sample is collected on a surface that carry antibodies that bind the cells. Antibodies may be covalently or non-covalently coupled to the surface by any suitable technique as is known in the art.

To carry out interpolation, it is preferable that the exogenous targets be in or on the chamber, or on the (generally planar, but not always perfectly planar) surface supporting the specimen or sample to be imaged, at a plurality of locations. While in some embodiments 3 locations will be sufficient, in other embodiments 4, 5, or 6 or more locations are desired. The locations may be separate and discrete from one another (that is, without exogenous target deposited therebetween) or may be contiguous (that is, with exogenous target therebetween). Spacing between the locations will in general be determined by factors such as magnification and the size of the sample to be imaged (particularly in the XY dimensions), but in some embodiments the locations will be spaced apart at least 10, 20, or 30 percent of the average width of the sample support surface or chamber to be imaged. Such spacing may be achieved by depositing the exogeneous targets at discrete locations around the region where the antibodies are deposited, by depositing the exogenous targets at discrete locations among the region where the antibodies are deposited, by depositing exogenous targets on at least a major portion, or all of, the support surface or chamber to be imaged, etc.

The foregoing is illustrative of the present invention, and is not to be construed as limiting thereof. The invention is defined by the following claims, with equivalents of the claims to be included therein.

That which is claimed is:

1. An XYZ stage assembly for securing a sample cartridge in an automated microscope having X, Y, and Z planes of movement, the XYZ stage assembly comprising:
   a sample cartridge having an end portion, a pair of generally parallel opposing side edge portions, and a locking edge portion formed thereon; and
   an XYZ stage, said XYZ stage comprising:
      a base member having a planar stage surface portion;
      a pair of generally parallel oppositely facing guide members on said planar stage surface portion and configured for slideably receiving said sample cartridge therebetween;
      a locking member on said planar stage surface portion and positioned to press against the sample cartridge locking edge portion when said sample cartridge is inserted between said pair of generally parallel oppositely facing guide members, so that pressure is exerted by said locking member through said sample cartridge against at least one of said pair of generally parallel oppositely facing guide members, whereby said sample cartridge is removably locked in place on the XYZ stage in the Z plane,
   wherein said locking member comprises a ball detent;
   wherein each pair of generally parallel opposing side edge portions has an upper corner portion, with said locking edge portion positioned at an angle in relation to both said pair of generally parallel opposing side edge portions and said end portion;
   wherein each of said pair of generally parallel oppositely facing guide members has an inwardly angled edge portion configured for contacting one of said sample cartridge upper corner portions when the sample cartridge is inserted therebetween;

wherein said XYZ stage further comprises: a terminal block member on said planar stage surface portion and positioned to contact the sample cartridge end portion when the sample cartridge is inserted between said pair of generally parallel oppositely facing guide members; and wherein said locking member on said planar stage surface portion is positioned to press against the sample cartridge locking edge portion at an angle in relation to both said pair of generally parallel opposing side edge portions and said end portion when said sample cartridge is inserted between said pair of generally parallel oppositely facing guide members and in contact with said terminal block member, so that pressure is exerted by said locking member through said sample cartridge edge portion against both said terminal block member and one of said pair of generally parallel oppositely facing guide members, whereby the sample cartridge is removably locked in place on the XYZ stage in all three of said X, Y and Z planes.

2. The XYZ stage assembly of claim 1, wherein said sample cartridge is further removably locked in place on the XYZ stage in an X, Y, and Z axes of rotation.

\* \* \* \* \*